United States Patent [19]
Bigge et al.

[11] Patent Number: 6,130,234
[45] Date of Patent: Oct. 10, 2000

[54] 4-SUBSTITUTED PIPERIDINE ANALOGS AND THEIR USE AS SUBTYPE SELECTIVE NMDA RECEPTOR ANTAGONISTS

[75] Inventors: Christopher F. Bigge; Jonathan Wright, both of Ann Arbor, Mich.; Sui Xiong Cai, Foothill, Calif.; Eckard Weber, Laguna Beach, Calif.; Richard Woodward, Aliso Viejo, Calif.; Nancy C. Lan, South Pasadena, Calif.; Zhang-Lin Zhou, Irvine, Calif.; John F. W. Keana, Eugene, Oreg.

[73] Assignees: Warner-Lambert Company, Morris Plains, N.J.; Cocensys, Incorporated, Irvine, Calif.

[21] Appl. No.: 09/091,594
[22] PCT Filed: Dec. 20, 1996
[86] PCT No.: PCT/US96/20766
§ 371 Date: Sep. 16, 1998
§ 102(e) Date: Sep. 16, 1998
[87] PCT Pub. No.: WO97/23214
PCT Pub. Date: Jul. 3, 1997

Related U.S. Application Data
[60] Provisional application No. 60/009,192, Dec. 22, 1995.

[51] Int. Cl.[7] ............... A61K 31/445; C07D 211/14; C07D 235/08
[52] U.S. Cl. ............... 514/322; 514/221; 514/255; 514/258; 514/311; 514/312; 514/321; 540/500; 540/506; 540/518; 544/283; 544/285; 544/349; 546/153; 546/197; 546/199; 546/201; 546/217; 546/223
[58] Field of Search ............... 540/500, 506, 540/518; 544/283, 285, 349; 546/153, 197, 199, 201, 217, 223; 514/221, 255, 258, 311, 312, 321, 322

[56] References Cited

U.S. PATENT DOCUMENTS

| | | | |
|---|---|---|---|
| 3,311,624 | 3/1967 | Phnacker et al. | 546/187 |
| 3,686,187 | 8/1972 | Cole et al. | 546/223 |
| 4,312,876 | 1/1982 | Klioze et al. | 546/216 |
| 4,567,187 | 1/1986 | Banno et al. | 546/157 |
| 4,577,020 | 3/1986 | Gall | 544/366 |
| 5,270,312 | 12/1993 | Glase et al. | 514/252 |

FOREIGN PATENT DOCUMENTS

| | | |
|---|---|---|
| 164633 | 12/1985 | European Pat. Off. . |
| 2539452 | 3/1976 | Germany . |

OTHER PUBLICATIONS

Praliev et al. "Synthesis of piperidine and decahydroquinoline derivatives . . . " CA 94:121260, 1980.

Praliev et al. "Synthesis of piperidine and decahydroquinoline derivatives . . . " CA 101:54881, 1983.

Yang et al. "Synthesis tnad anesthetic activity of 3–methyl fentanyl derivatives" CA 120:323214, 1993.

B.L. Chenard, et al., J. Med. Chem. 34, 3085–3090 (1991).

S.A. Glase, et al., J. Med. Chem. 39, 3179–3187 (1996).

*Primary Examiner*—Ceila Chang
*Attorney, Agent, or Firm*—Fitzpatrick, Cella, Harper & Scinto

[57] ABSTRACT

Novel 4-substituted piperidine analogs, pharmaceutical compositions containing the same and the method of using 4-substituted piperidine analogs as selectively active antagonists of N-methyl-D-aspartate (NMDA) receptor subtypes for treating conditions such as stroke, cerebral ischemia, central nervous system trauma, hypoglycemia, anxiety, convulsions, aminoglycoside antibiotics-induced hearing loss, migraine headaches, glaucoma, CMV retinitis, chronic pain, opioid tolerance or withdrawals, or neurodegenerative disorders, such as lathyrism, Alzheimer's Disease, Parkinsonism and Huntington's Disease are described. Also described are novel methods for preparing 4-substituted piperidine analogs and novel intermediates of the 4-substituted piperidine analogs.

16 Claims, No Drawings

4-SUBSTITUTED PIPERIDINE ANALOGS AND THEIR USE AS SUBTYPE SELECTIVE NMDA RECEPTOR ANTAGONISTS

This application claims benefit of provisional application 60/009,192, filed Dec. 22, 1995.

BACKGROUND OF THE INVENTION

1. Field of the Invention

This invention is related to 4-substituted piperidine analogs, including hydroxypiperidine and tetrahydropyridine analogs, as well as novel intermediates of the 4-substituted analogs. The analogs are selectively active as antagonists of N-methyl-D-aspartate (NMDA) receptor subtypes. The invention is also directed to the use of 4-substituted piperidine analogs as neuroprotective agents for treating conditions such as stroke, cerebral ischemia, central nervous system trauma, hypoglycemia, anxiety, convulsions, aminoglycoside antibiotics-induced hearing loss, migraine headache, chronic pain, glaucoma, CMV retinitis, psychosis, urinary incontinence, opioid tolerance or withdrawal, or neuro-degenerative disorders such as lathyrism, Alzheimer's Disease, Parkinsonism and Huntington's Disease.

2. Related Background Art

Excessive excitation by neurotransmitters can cause the degeneration and death of neurons. It is believed that this degeneration is in part mediated by the excitotoxic actions of the excitatory amino acids (EAA) glutamate and aspartate at the N-methyl-D-Aspartate (NMDA) receptor. This excitotoxic action is considered responsible for the loss of neurons in cerebrovascular disorders such as cerebral ischemia or cerebral infarction resulting from a range of conditions, such as thromboembolic or hemorrhagic stroke, cerebral vasospasms, hypoglycemia, cardiac arrest, status epilepticus, perinatal asphyxia, anoxia such as from drowning, pulmonary surgery and cerebral trauma, as well as lathyrism, Alzheimer's Disease, Parkinson's Disease and Huntington's Disease.

Various classes of substituted piperidine analogs are known. For example, U.S. Pat. No. 5,273,977 generically discloses tetrahydropyridine and hydroxy piperidine derivatives described by the formula:

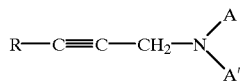

wherein n is an integer of 2, 3, or 4; Z is

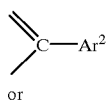

or

$Ar^1$ and $Ar^2$ are each independently substituted or unsubstituted aryl, a heteroaromatic ring, or a heteroaromatic bicylic ring. The tetrahydropyridines and hydroxypiperidines of this reference are indicated to be useful as central nervous system agents, particularly as dopaminergic, antipsychotic and antihypertensive agents, and for treating central nervous system disorders such as Parkinson Disease, Huntington Disease and depression. The particular 4-substituted piperidines, including the 4-hydroxypiperdines and tetrahydropyridines of this invention are not exemplified. In addition, there is no disclosure or suggestion of treating disorders with selective NMDA receptor subtype antagonists and the advantages of such treatment.

GB 1055548 discloses 1-aryl-3-aminopropynes having the generic formula:

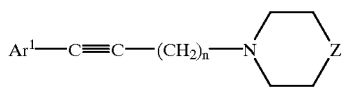

wherein R represents unsubstituted phenyl or phenyl substituted by methyl, halogen, nitro, amino, (lower alkanoyl) amino, or lower alkoxyl; and either A is alkyl of 1 to 4 carbon atoms and A' is alkyl of 1 to 4 carbon atoms, benzyl, chlorobenzyl, or dimethoxybenzyl; or A and A', together with the adjacent nitrogen atom, from one of the following heterocyclic rings: pyrrolidino, 25 morpholino, thiomorpholino, 4-phenylpiperidino, 4-phenyl-4-hydroxypiperidino, N'-methylpiperazino, N'-benzylpiperazino, N'-phenylpiperazino, N'-chlorophenylpiperazino, N'-tolylpiperazino, N'-methoxyphenylpiperamino, N'-(β-hydroxyethyl) piperazino, N'-(β-acetoxyethyl)piperazino, N'-(β-propionyloxyethyl)-piperazino, N'-carbethoxypiperazino, hexamethyleneimino, and heptamethylene-imino; provided that when R is phenyl, p-methoxyphenyl, o- or p-nitrophenyl, or o-aminophenyl,

does not represent dimethylamino or diethylamino; and their acid addition salts, especially those containing physiologically innocuous anions. The compounds of this reference are said to have antiulcer activity. This reference does not disclose or suggest the 4-substituted piperidine analogs of this invention or their use as selective NMDA receptor subtype antagonists.

DE 3703435 discloses compounds having a piperidine ring substituted by an aminothiazole moiety. The compounds are said to be useful for treating Parkinson's Disease, schizophrenia and circulatory disorders with a particular effect on the dopaminergic system. This reference does not disclose or suggest the compositions of the present invention, let alone their use as selective NMDA receptor subtype antagonists.

PCT International Publication Number WO 92/02502 generically discloses N-hydrocarbyl 4-substituted piperidines described by the formula:

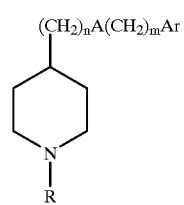

in which

R is $C_{1-8}$alkyl(phenyl)p, $C_{2-8}$alkenyl(phenyl)p, $C_{2-8}$alkynyl(phenyl)p, $C_{3-8}$cycloalkyl;

p is 0 to 2;
n is 0 to 6;
A is a bond, oxygen, sulphur or $NR^1$;
$R^1$ is hydrogen, $C_{1-8}$alkyl or phenyl$C_{1-4}$alkyl;
m is 0 to 3; and
Ar is aryl or heteroaryl, each of which may be optionally substituted; and salts thereof.

This reference exemplifies 4-aryloxyalkyl piperidines. The substituted piperidines are said to be calcium channel blockers expected to be useful in the treatment of anoxia, ischemia including stroke, migraine, epilepsy, traumatic head injury, AIDS-related dementia, neurodegenerative disorders and drug addiction. The reference does not disclose or suggest the particular 4-substituted piperidine analogs of this invention or their use as selective NMDA receptor subtype antagonists for the treatment of disorders responsive thereto.

PCT International Publication Number WO 93/15052 generically describes compounds that are said to be calcium channel antagonists broadly represented by the formula:

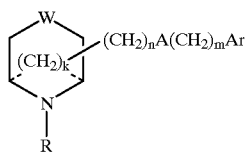

and the salts thereof, wherein W is —$CH_2$—, a bond, O or S; k is O, or when W represents —$CH_2$— k may also be 2, in which case the dotted lines represent single bonds;
R is $C_{1-8}$alkyl(phenyl)p, $C_{2-8}$alkenyl(phenyl)p, $C_{2-8}$alkynyl(phenyl)p, $C_{3-8}$cycloalkyl or $C_{1-8}$alkyl$C_{3-8}$cycloalkyl, or R may also represent hydrogen when k is 2;
p is 0 to 2 n is 0 to 6;
m is 0 to 6; and
A is a bond, —CH=CH—, —C≡C—, oxygen, sulphur or $NR^1$;
$R^1$ is hydrogen, $C_{1-8}$alkyl or phenyl$C_{1-4}$alkyl; and
Ar is aryl or heteroaryl, each of which may be optionally substituted; provided that: when W is a bond the side chain is α to the ring nitrogen atom; when W is $CH_2$, k is zero, the side chain is at the 3- or 4-position of the piperidine ring and A is a bond, oxygen, sulphur or $NR^1$ then Ar is aryl substituted by phenoxy or substituted phenoxy or is a tricyclic heteroaryl group as hereinafter defined; and when W is $CH_2$ and k is 2 the side chain —$(CH_2)_nA(CH_2)_m$Ar is not α to the nitrogen atom. This reference exemplifies mostly 2 and 3 substituted piperidines. In addition, the particular group of 3 and 4 substituted piperidines described by the reference requires A to be —CH=CH— or —C≡C—. This reference does not disclose or suggest the 4-substituted piperidine analogs of this invention. Moreover, there is no suggestion of employing 4-substituted piperidine analogs as selective NMDA receptor subtype antagonists.

EP 0235463 discloses N-substituted-arylalkyl and arylalkylene aminoheterocyclics as coronary vasodilators, antihypertensives, antiarrhythmic, antiallergy, antihistamic and antisecretory agents. 4-substituted N-alkene and alkyne piperidine analogs of this invention, as well as their NMDA antagonistic activity, are not disclosed or suggested.

U.S. Pat. No. 5,169,855 generically discloses disubstituted piperidine ether derivatives for use as antipsychotic agents selective for sigma receptors. Similarly, PCT International Publication No. WO 92/18127 and PCT International Publication No. WO 91/06297 generically disclose N-phthalimidoalkyl piperidines which are useful as antipsychotic agents and which are selective for sigma receptors.

However, the 4-substituted piperidine analogs of this invention are not disclosed by these references and there is no mention of NMDA receptor activity.

Numerous references have disclosed additional piperidine derivatives substituted at the 4 and 3 position for use in a variety of treatments. Such references include, for example, U.S. Pat. No. 3,255,196 (3 and 4-substituted piperidines that are active antitussives and possess analgesic, antiemetic and local anaesthetic properties); U.S. Pat. No. 5,202,346 (4-substituted piperidines that are Class III antiarrhythmic agents); PCT International Publication No. WO 88/02365 (3 and 4-substituted piperidines that may be useful for treatment of mental disorders accompanying cerebrovascular disease); BE 860701 (4-substituted piperidines for use as vasodilators and β-adrenergic inhibitors); FR 2681319 (4-substituted piperidines for use as neuroprotectors and anticonvulsants); and DE 2939292 (4-substituted piperidines for use as antiallergenic and antiinflammatory agents). None of these references disclose or suggest the 4-substituted piperidine analogs of the present invention or their use as selective NMDA receptor subtype antagonists.

Excitatory amino acid receptor antagonists that block NMDA receptors are recognized for usefulness in the treatment of disorders. NMDA receptors are intimately involved in the phenomenon of excitotoxicity, which may be a critical determinant of outcome of several neurological disorders. Disorders known to be responsive to blockade of the NMDA receptor include acute cerebral ischemia (stroke or cerebral trauma, for example), muscular spasm, convulsive disorders, neuropathic pain and anxiety, and may be a significant causal factor in chronic neurodegenerative disorders such as Parkinson's disease [T. Klockgether, L. Turski, Ann. Neurol. 34, 585–593 (1993)], human immunodeficiency virus (HIV) related neuronal injury, amyotrophic lateral sclerosis (ALS), Alzheimer's disease [P. T. Francis, N. R. Sims, A. W. Procter, D. M. Bowen, J. Neurochem. 60 (5), 1589–1604 (1993)] and Huntington's disease. [See S. Lipton, TINS 16 (12), 527–532 (1993); S. A. Lipton, P. A. Rosenberg, New Eng. J. Med. 330 (9), 613–622 (1994); and C. F. Bigge, Biochem. Pharmacol. 45, 1547–1561 (1993) and references cited therein.]. NMDA receptor antagonists may also be used to prevent tolerance to opiate analgesia or to help control withdrawal symptoms from addictive drugs (Eur. Pat. Appl. 488,959A).

Expression cloning of the first NMDA receptor subunit, NMDAR1 (NR1) in Nakanishi's lab in 1991 provided an initial view of the molecular structure of the NMDA receptor [Nature 354, 31–37 (1991)]. There are several other structurally related subunits (NMDAR2A through NMDAR2D) that join NR1 in heteromeric assemblies to form the functional ion channel complex of the receptor [Annu. Rev. Neurosci. 17, 31–108 (1994)]. The molecular heterogeneity of NMDA receptors implies a future potential for agents with subtype selective pharmacology.

Many of the properties of native NMDA receptors are seen in recombinant homomeric NR1 receptors. These properties are altered by the NR2 subunits. Recombinant NMDA receptors expressed in Xenopus oocytes have been studied by voltage-clamp recording, as has developmental and regional expression of the mRNAs encoding NMDA receptor subunits. Electrophysiological assays were utilized to characterize the actions of compounds at NMDA receptors expressed in Xenopus oocytes. The compounds were assayed at three subunit combinations of cloned rat NMDA receptors, corresponding to four putative NMDA receptor subtypes [Moriyoshi, et al. Nature 1991, 354, 31–37; Monyer et al, Science 1992, 256, 1217–1221; Kutsuwada et al, Nature 1992, 358, 36–41; Sugihara et al, Biochem. Biophys Res. Commun. 1992, 185, 826–832].

An object of this invention is to provide novel 4-substituted piperidine analogs which function as subtype-selective NMDA receptor antagonists.

A further object of this invention is to provide a pharmaceutical composition containing an effective amount of the 4-substituted piperidine analogs to treat cerebrovascular disorders responsive to the selective blockade of NMDA receptor subtypes.

Another object of this invention is to provide a method of treating disorders responsive to the subtype-selective NMDA receptor antagonists in an animal by administering a pharmaceutically effective amount of 4-substituted piperidine analogs.

Yet another object of this invention is to provide novel methods of preparing 4-substituted piperidine analogs.

A further object of this invention is directed to novel intermediates of the 4-substituted piperidine analogs of this invention.

SUMMARY OF THE INVENTION

This invention relates to novel 4-substituted piperidine analogs represented by the formula (I):

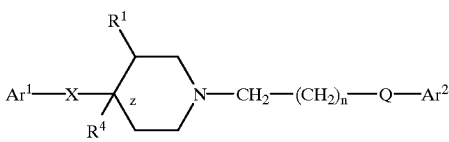

I or a pharmaceutically acceptable salt thereof wherein $Ar^1$ and $Ar^2$ are independently aryl or a heteroaryl group, either of which may be independently substituted by hydrogen, hydroxy, alkyl, halogen, nitro, aryl, aralkyl, amino, a halogenated alkyl group, —NHAc, —NHSO$_2$Me, —N(SO$_2$Me)$_2$, —CONHalkyl, —SO$_2$NH$_2$, an alkylguanidine group, a lower alkyl amino group or a lower alkoxy group;

z is a single or double bond;

X is —(CHR$^2$)$_m$—, O, S or NR$^3$, wherein each $R^2$ is independently hydrogen, hydroxy, lower alkoxy or a lower alkyl group having 1 to 6 carbon atoms and m is 0, 1 or 2, and $R^3$ is hydrogen or a lower alkyl group having 1 to 6 carbon atoms, provided that when z is a double bond then X is not O, S or NR$^3$;

$R^1$ is hydrogen or hydroxy;

n is 0, 1 or 2;

Q is —CH═CH— or —C≡C—; and $R^4$ is hydrogen or hydroxy when z is a single bond provided that (i) when n is 0, then z is a double bond and $R^4$ is not present, (ii) when n is 1 or 2 and Q is —C≡—C— and z is a double bond or $R^4$ is hydroxy, then $Ar^1$ is aryl substituted by halogen and (iii) when $R^4$ is hydroxy then $R^2$ is not hydroxy or lower alkoxy.

The compounds of the present invention may exist as optical isomers and the inventive compounds include both the racemic mixtures of such optical isomers as well as the individual enantiomers.

Examples of pharmaceutically acceptable addition salts include inorganic and organic acid addition salts such as the hydrochloride, hydrobromide, phosphate, sulphate, citrate, lactate, tartrate, maleate, fumarate, mandelate, oxalate, and the acetate.

Halogen is fluorine, chlorine, bromine, or iodine; fluorine, chlorine, and bromine are preferred groups.

Alkyl means a straight or branched chain of from one to six carbon atoms or cyclic alkyl of from three to seven carbon atoms including, but not limited to methyl, ethyl, propyl, isopropyl, butyl, isobutyl, t-butyl, pentyl, hexyl, cyclopropyl, cyclobutyl, cyclopentyl, and cyclohexyl.

Aryl means a monocyclic or bicyclic carbocyclic aromatic ring system which can be substituted or unsubstituted, for example, but not limited to phenyl, naphthyl or the like.

Heteroaryl means a monocyclic or bicyclic carbocyclic aromatic ring system substituted by one or more hetero atoms, which can be the same or different, and includes, for example, thienyl, benzo[b]thienyl, naphtho[2,3[b]thienyl, thianthrenyl, furyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, 5aH-carbozolyl, carbozolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, quinoxalinyl, 2,3-dioxoquinoxalinyl, benzimidazolyl, 2-oxobenzimidazolyl, 2-oxindolyl and 2-thiobenzimidazolyl groups.

Aralkyl means any of the alkyl groups defined herein substituted by any of the aryl groups as defined herein.

Halogenated alkyl means any of the alkyl groups defined herein substituted by one or more halogen groups as defined herein.

Alkylguanidine means a guanidine substituted by one of the alkyl groups defined herein.

Lower alkyl amino means any of the alkyl groups defined herein substituted by an amino group.

Lower alkoxy means an alkoxy group containing an alkyl group as defined herein.

The instant invention is also related to a pharmaceutical composition containing the compound defined by formula I in an amount effective to treat cerebrovascular disorders responsive to the selective blockade of NMDA receptor subtypes and a pharmaceutically acceptable carrier. Exemplary disorders responsive to such treatment include cerebral ischemia caused by cerebral trauma, stroke, hypoglycemia, heart attack, and surgery; anxiety, psychosis and schizophrenia; glaucoma; CMV retinitis; urinary incontinence; opioid tolerance or withdrawal; and chronic neurodegenerative disorders such as Huntington's disease, ALS, Parkinsonism and Alzheimer's disease. The pharmaceutical composition of this invention may also be employed as an analgesic or for the treatment of epilepsy or migraine headaches.

The invention is also related to a method for preparing the compound of formula (I) comprising the steps of:

(a) reacting, in the presence of a base, a compound of formula VII

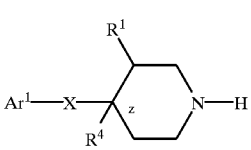

VII wherein $Ar^1$, X, $R^1$, $R^4$ and z are as previously described, with a compound of formula IX

L—CH$_2$—(CH$_2$)$_n$—Q—H      IX wherein n and Q are as previously described and L is a leaving group to afford a compound of formula X

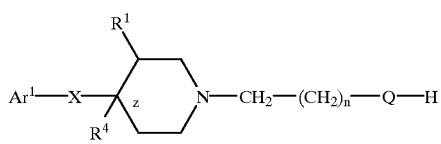

wherein Ar¹, X, R¹, R⁴, z, n and Q are as previously described; and (b) reacting the compound of formula X with Ar²Y, wherein Ar² is as previously defined and Y is a transmetalation group, such as for example, Br, I, B(OH)₂ or HgCl, in the presence of a palladium catalyst to afford the compound of formula I. The leaving group L is preferably selected from the group consisting of para-toluenesulfonate, halogen, triflate and the like. Para-toluenesulfonate is most preferred. The transmetalation group is a group capable of transmetalating with palladium.

The base used in step (a) of the above described process is generally present in at least an amount equivalent to the tosylate of formula IX to ensure that the tosic acid evolved during the reaction is quenched. Such bases include, for example, triethylamine, potassium carbonate or the like. The reaction of step (a) is conducted in a polar aprotic solvent, such as, for example, tetrahydrofuran, dimethylformamide, acetonitrile or the like. The reaction generally may be conducted at temperature between ambient temperature and 100° C., although the temperature is typically not critical.

The reaction of step (b) is conducted typically in the presence of a palladium catalyst such as PdCl₂(PPh₃)₂, i.e., bis(triphenyl-phosphine)palladium(II)chloride and a base such as, for example, triethylamine. The reaction of this step is generally run at a temperature from about 60 to about 100° C. in a polar solvent such as tetrahydrofuran, methanol, acetonitrile, t-butylamine or the like. The resulting product may be purified by means well known to those of ordinary skill in the art.

Yet another method of this invention for preparing the compound of formula (I) comprises the steps of: (a) reacting, in the presence of a palladium catalyst, a compound of formula XI

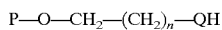     XI wherein P is a general protecting group, and n and Q are as previously described, with Ar²Y, wherein Ar² is as previously defined and Y is a transmetalating group, such as for example Br, I, B(OH)₂ or HgCl, to afford a compound represented by formula XII

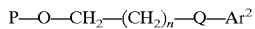     XII wherein P, n, Q and Ar₂ are as previously described;

(b) deprotecting the compound of formula XII to give a compound represented by formula XIII

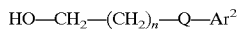     XIII wherein n, Q and Ar² are as previously described;

(c) reacting the compound of formula XIII with an activating compound such as tosylates e.g., tosylchloride, mesylates triflates, diethylazadicarboxylates or the like in the presence of base, to give the compound represented by formula XIV

     XIV wherein A is an activating group such as, for example, a para-toluenesulfonate group, and n, Q and Ar² are as previously described; and (d) reacting, in the presence of a base, the compound of formula XIV with the compound of formula VII

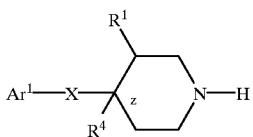     VII wherein Ar¹, X, R¹, R⁴ and z are as previously described, to give the compound of formula I.

The general protecting group P of this method of the invention is, for example, selected from the group consisting of t-butyldimethylsilyl, methoxymethyl, tetrahydropyranyl, trimethylsilyl and the like, with the silyl protecting groups preferred. The palladium catalyst employed in step (a) of this method may be, for example, PdCl₂(PPh₃)₂. Generally this step of the reaction is conducted in the presence of a base, such as triethylamine, at a temperature range of 60–100° C. in a polar solvent, such as tetrahydrofuran, methanol, acetonitrile, t-butylamine or the like.

Step (d) of this method is also performed in the presence of a base, such as triethylamine or potassium carbonate, to ensure that the tosic acid evolved during the reaction is quenched. This reaction step (d) is performed in an aprotic polar solvent, such as tetrahydrofuran, dimethylformamide, acetonitrile or the like at a temperature typically between ambient temperature and about 100° C. The resulting product may be purified by means well known to one of ordinary skill in the art.

This invention is further directed to novel intermediates which may be prepared during the preparation of the 4-substituted piperidine analogs of this invention. These novel intermediates also possess NMDA subtype selective activity.

The novel intermediate compounds are represented by the formula (X):

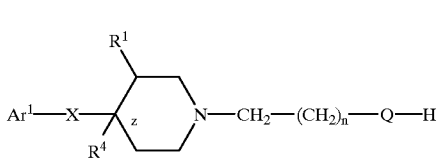     (X)

or a salt thereof, wherein

Ar¹ is aryl or a heteroaryl group, either of which may be independently substituted by hydrogen, hydroxy, alkyl, halogen, nitro, aryl, aralkyl, amino, a halogenated alkyl group, —NHAc, —NHSO₂Me, —N(SO₂Me)₂, —CONHalkyl, —SO₂NH₂, a lower alkyl amino group or a lower alkoxy group;

z is a single or double bond;

X is —(CHR²)ₘ—, O, S or NR³, wherein each R² is independently hydrogen, hydroxy, lower alkoxy or a lower alkyl group having 1 to 6 carbon atoms and m is 0, 1 or 2, and R³ is hydrogen or a lower alkyl group having 1 to 6 carbon atoms, provided that when z is a double bond then X is not O, S or NR²;

Q is —CH=CH— or —C≡C—;

R¹ is hydrogen or hydroxy; and

R⁴ is hydrogen or hydroxy when z is a single bond, provided that (i) when X is —(CHR²)ₘ—, m is 0 and Q is —C≡C— then z is not a double bond and (ii) when R⁴ is hydroxy then R² is not hydroxy or lower alkoxy.

The invention further relates to a method for treating disorders responsive to the selective blockade of N-methyl-D-aspartate receptor subtypes in an animal suffering thereof which comprises administering in unit dosage form at least one compound represented by the formula (I):

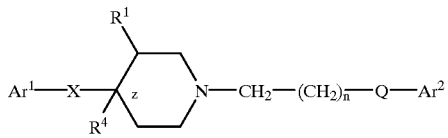

(I)

or a pharmaceutically acceptable salt thereof wherein $Ar^1$ and $Ar^2$ are independently aryl or a heteroaryl group, either of which may be independently substituted by hydrogen, alkyl, halogen, hydroxy, nitro, aryl, aralkyl, amino, a halogenated alkyl group, —NHAc, —NHSO$_2$Me, —N(SO$_2$Me)$_2$, —CONHalkyl, —SO$_2$NH$_2$, an alkylguanidine group, a lower alkyl amino group or a lower alkoxy group;

z is a single or double bond;

X is —(CHR$^2$)$_m$—, O, S or NR$^3$, wherein $R^2$ is independently hydrogen, hydroxy, lower alkoxy or a lower alkyl group having 1 to 6 carbon atoms and m is 0, 1 or 2, and $R^3$ is hydrogen or a lower alkyl group having 1 to 6 carbon atoms provided that when z is a double bond then X is not O, S or NR$^3$;

$R^1$ is hydrogen or hydroxy;

n is 0, 1 or 2;

Q is —CH=CH— or —C≡C—; and $R^4$ is hydrogen or hydroxy when z is a single bond, provided that when $R^4$ is hydroxy then $R^2$ is not hydroxy or lower alkoxy. The invention also relates to a method for treating disorders responsive to the selective blockade of N-methyl-D-aspartate receptor subtypes in an animal suffering thereof comprising administering in unit dosage form at least one intermediate compound represented by the formula (X).

DETAILED DESCRIPTION OF THE INVENTION

The novel 4-substituted piperidine analogs of this invention are represented by previously defined formula (I). Generally, Q is preferably —C≡C—. In addition, $Ar^2$ is preferably a pyridynyl or a phenyl group unsubstituted or substituted by halogen, amino or a lower alkyl amino group. Preferably $Ar^1$ is phenyl, more preferably phenyl substituted by a halogen group and most preferably 4-chlorophenyl.

Preferred embodiments of the novel 4-substituted piperidine analogs of this invention are represented by formula (II–VII). In particular, a first embodiment is represented by formula (II) as follows:

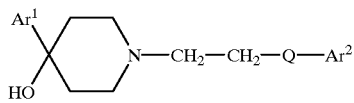

(II)

or a pharmaceutically acceptable salt thereof wherein:

$Ar^1$ and $Ar^2$ are independently aryl or a heteroaryl group, either of which may be independently substituted by hydrogen, hydroxy, alkyl, halogen, nitro, aryl, aralkyl, amino, a halogenated alkyl group, —NHAc, —NHSO$_2$Me, —N(SO$_2$Me)$_2$, —CONHalkyl, —SO$_2$NH$_2$, an alkylguanidine group, a lower alkyl amino group or a lower alkoxy group; and Q is —CH=C— or —C≡C—, provided that when Q is —C≡C— then $Ar^1$ is aryl substituted by halogen. Preferably, when Q is —C≡C— then $Ar^2$ is substituted by amino.

Another embodiment of the novel 4-substituted piperidines of this invention is represented by formula (III) as follows:

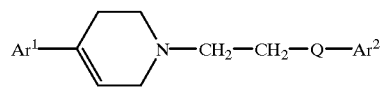

(III)

or a pharmaceutically acceptable salt thereof wherein;

$Ar^1$ and $Ar^2$ are independently aryl or a heteroaryl group, either of which may be independently substituted by hydrogen, hydroxy, alkyl, halogen, nitro, aryl, aralkyl, amino, a halogenated alkyl group, —NHAc, —NHSO$_2$Me, —N(SO$_2$Me)$_2$, —CONHalkyl, —SO$_2$NH$_2$, an alkylguanidine group, a lower alkyl amino group or a lower alkoxy group; and Q is —CH=CH— or —C≡C—, provided that when Q is —C≡C— then $Ar^1$ is aryl substituted by halogen. Preferably, when Q is —C≡C— then $Ar^2$ is substituted by an amino or hydroxy group.

Three additional embodiments of the novel 4-substituted piperidines of this invention are represented by formula (IV–VI) as follows:

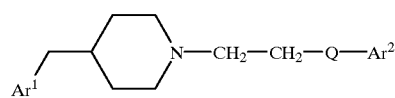

(IV)

or a pharmaceutically acceptable salt thereof,

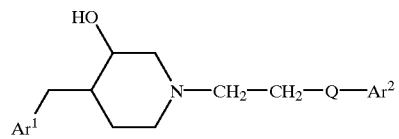

(V)

or a pharmaceutically acceptable salt thereof, or

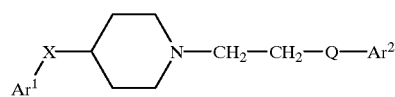

(VI)

or a pharmaceutically acceptable salt thereof, wherein:

$Ar^1$ and $Ar^2$ are independently aryl or a heteroaryl group, either of which may be independently substituted by hydrogen, hydroxy, alkyl, halogen, nitro, aryl, aralkyl, amino, a halogenated alkyl group, —NHAc, —NHSO$_2$Me, —N(SO$_2$Me)$_2$, —CONHalkyl, —SO$_2$NH$_2$, an alkylguanidine group, a lower alkyl amino group or a lower alkoxy group; and Q is —CH=CH— or —C≡C—. For formula (VI) X is O or S.

Yet another embodiment of the invention is represented by the formula (VII):

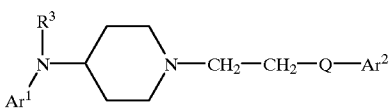

(VII)

or a pharmaceutically acceptable salt thereof wherein:

Ar$^1$ and Ar$^2$ are independently aryl or a heteroaryl group, either of which may be independently substituted by hydrogen, alkyl, halogen, nitro, aryl, aralkyl, amino, a halogenated alkyl group, —NHAc, —NHSO$_2$Me, —N(SO$_2$Me)$_2$, —CONHalkyl, —SO$_2$NH$_2$, an alkylguanidine group, a lower alkyl amino group or a lower alkoxy group; and Q is —CH=CH- or —C≡C—; and R$^3$ is hydrogen or a lower alkoxy group having 1 to 6 carbon atoms.

Exemplary preferred compounds of formula I include, without limitation:

** 1-[4-(3-aminophenyl)-3-butynyl]-4-hydroxy-4-(4-chlorophenyl)piperidine;
** 1-[4-(5-(2-amino)pyridynyl)-3-butynyl]-4-hydroxy-4-(4-chlorophenyl)piperidine;
* 1-[4-(4-fluorophenyl)-3-butynyl]-4-hydroxy-4-(4-chlorophenyl)piperidine;
* 1-[5-(3-aminophenyl)-4-pentynyl]-4-hydroxy-4-(4-hlorophenyl)piperidine;
** 1-[4-(3-aminophenyl)-3-butynyl]-4-(4-chlorophenyl)-1,2,5,6-tetrahydropyridine;
** 1-[4-(5-(2-amino)pyridynyl)-3-butynyl]-4-(4-chlorophenyl)-1,2,5,6-tetrahydropyridine;
* 1-[4-(4-fluorophenyl)-3-butynyl]-4-(4-chlorophenyl)-1,2,5,6-tetrahydropyridine;
* 1-[5-(3-aminophenyl)-4-pentynyl]-4-(4-chlorophenyl)-1,2,5,6-tetrahydropyridine;
* 4-Benzyl-1-[4-(3-aminophenyl)-3-butynyl]piperidine;
4-Benzyl-1-(4-phenyl-3-butynyl)piperidine;
** 4-(4-Chloro)benzyl-1-[4-(3-aminophenyl)-3-butynyl]piperidine;
** 4-(4-Chloro)benzyl-1-[4-(4-hydroxyphenyl-3-butynyl]pipridine
** 4-(4-chloro)benzyl-1-[4-(5-(2-amino)pyridynyl)-3-butynyl]-piperidine;
* 1-[4-(4-fluorophenyl)-3-butynyl]-4-(3-trifluoromethylbenzyl)-piperidine;
* 4-(4-chlorobenzyl)-1-[5-(3-aminophenyl)-4-pentynyl]-piperidine;
*4-Benzyl-1-[4-(3-aminophenyl)-3-butynyl]-3-hydroxypiperidine;
4-Benzyl-1-(4-phenyl-3-butynyl)-3-hydroxypiperidine;
** 4-(4-Chloro)benzyl-1-[4-(3-aminophenyl)-3-butynyl]3-hydroxypiperidine;
** 4-(4-chloro)benzyl-1-[4-(5-(2-amino)pyridynyl)-3-butynyl]-3-hydroxypiperidine;
* 1-[4-(4-fluorophenyl)-3-butynyl]-4-(3-trifluoromethylbenzyl)-3-hydroxy-piperidine;
* 4-(4-chlorobenzyl)-3-hydroxy-1-[5-(3-aminophenyl)-4-pentynyl]-piperidine;
* 1-[4-(3-aminophenyl)-3-butynyl]-4-phenoxy-piperidine;
1-(4-phenyl-3-butynyl)-4-phenoxypiperidine;
** 1-[4-(3-aminophenyl)-3-butynyl]-4-(4-chloro)phenoxypiperidine;
** 1-[4-(5-(2-amino)pyridynyl)-4-butynyl]-4-(4-chloro)phenoxypiperidine;
* 1-[4-(4-fluorophenyl)-3-butynyl]-4-(3-trifluoromethyl)phenoxypiperidine;
* 1-[5-(3-aminophenyl)-4-pentynyl]-4-(4-chloro)phenoxypiperidine;
* 1-[4-(3-aminophenyl)-3-butynyl]-4-(phenyl)aminopiperidine;
1-(4-phenyl-3-butynyl)-4-(phenyl)aminopiperidine;
** 1-[4-(3-aminophenyl)-3-butynyl]-4-(4-chlorophenyl)aminopiperidine;
** 1-[4-(5-(2-amino)pyridynyl)-3-butynyl]-4-(4-chlorophenyl)aminopiperidine;
* 1-[4-(4-fluorophenyl)-3-butynyl]-4-(3-trifluoromethylphenyl)aminopiperidine;
* 4-phenyl-1-(4-phenyl-3-butynyl)piperidine;
4-(3-(trifluoromethyl)phenyl)-3-hydroxy-1-(4-phenyl-3-butynyl)piperidine;
* 1-(4-(4-aminophenyl)-3-butynyl)-4-(4-chlorophenyl)-4-hydroxypiperidine;
N-n-butyl-N'-(3-(4-(4-chlorophenyl)-4-hydroxy)piperidinyl)butynyl)phenylguanidine;
** 4-benzyl-1-(4-(3-methylphenyl)-3-butynyl)piperidine;
** 1-(4-(4-aminophenyl)-3-butynyl)-4-benzylpiperidine;
** 1-(4-(4-aminophenyl)-3-butynyl)-4-(4- chlorobenzyl)piperidine;
** 1-(4-(4-amino-3-fluorophenyl)-3-butynyl)-4-(4-chlorobenzyl)piperdine;
N-4-(1-(4-(3-aminophenyl)butyn-3-yl)piperidinyl)-2-oxobenzimidazol;
** 1-(4-(2-aminophenyl)-3-butynyl)-4-phenylpiperidine; and
* 1-[5-(3-aminophenyl)-4-pentynyl]-4-(4-chlorophenyl)aminopiperidine;
4-{4-[4-(4-Chloro-phenoxy)-piperidin-1-yl]-but-1-ynyl}-phenylamine;
N-{4-[4-(4-Phenoxy-piperidin-1-yl)-but-1-ynyl]-phenyl}-acetamide;
4-{4-[4-(4-Methyl-benzyl)-piperidin-1-yl]-but-1-ynyl}-phenylamine;
4-Benzyl-1-[4-(4-nitro-phenyl)-but-3-ynyl]-piperidine;
4-Benzyl-1-[4-(4-methoxy-phenyl)-but-3-ynyl]-piperidine;
4-[4-(4-Benzyl-piperidin-1-yl)-but-1-ynyl]-phenol;
4-Benzyl-1-[4-(4-fluoro-phenyl)-but-3-ynyl]-piperidine;
4-Benzyl-1-[4-(4-chloro-phenyl)-but-3-ynyl]-piperidine;
4-Benzyl-1-[4-(3-chloro-phenyl)-but-3-ynyl]-piperidine;
4-Benzyl-1-[4-(2,3-dichloro-phenyl)-but-3-ynyl]-piperidine;
4-Benzyl-1-[4-(3,4-dichloro-phenyl)-but-3-ynyl]-piperidine;
4-Benzyl-1-(4-p-tolyl-but-3-ynyl)-piperidine;
4-Benzyl-1-[4-(2,3-dimethyl-phenyl)-but-3-ynyl]-piperidine;
4-Benzyl-1-[4-(3,4-dimethyl-phenyl)-but-3-ynyl]-piperidine;
3-[4-(4-Benzyl-piperidin-1-yl)-but-1-ynyl]-phenylamine;
3-[4-(4-Benzyl-piperidin-1-yl)-but-1-ynyl]-benzylamine;
N-{4-[4-(4-Benzyl-piperidin-1-yl)-but-1-ynyl]-phenyl}-acetamide;
{4-[4-(4-Benzyl-piperidin-1-yl)-but-1-ynyl]-phenyl}-methyl-amine;
{4-[4-(4-Benzyl-piperidin-1-yl)-but-1-ynyl]-phenyl}-dimethyl-amine;
N-{4-[4-(4-Benzyl-piperidin-1-yl)-but-1-ynyl]-phenyl}-methanesulfonamide;
4-[4-(4-Benzyl-piperidin-1-yl)-but-1-ynyl]-benzamide;
N-(Methylsulfonyl)-N-[4-[4-[4-(phenylmethyl)-1-piperidinyl]-1-butynyl]phenyl]-methanesulfonamide;
4-[4-(4-Benzyl-piperidin-1-yl)-but-1-ynyl]-benzenesulfonamide;
4-[4-(4-Benzyl-piperidin-1-yl)-but-1-ynyl]-N-butyl-benzamide;

1-(4-Benzo[1,3]dioxol-5-yl-but-3-ynyl)-4-benzyl-piperidine;
4-Benzyl-1-[4-(2,3-dihydro-benzo[1,4]dioxin-6-yl)-but-3-ynyl]-piperidine;
4-[3-(4-Benzyl-piperidin-1-yl)-prop-1-ynyl]-phenylamine;
N-{4-[3-(4-Benzyl-piperidin-1-yl)-prop-1-ynyl]-phenyl}-methanesulfonamide;
N-{4-[4-(4-Phenylsulfanyl-piperidin-1-yl)-but-1-ynyl]-phenyl}-acetamide;
5-[4-(4-Benzyl-piperidin-1-yl)-but-1-ynyl]-1H-indole;
4-{4-[4-(4-Methyl-benzyl)-piperidin-1-yl]-but-1-ynyl}-phenol;
5-[4-(4-Benzyl-piperidin-1-yl)-but-1-ynyl]-1H-indazole;
4-[4-(4-Benzyl-piperidin-1-yl)-but-1-ynyl]-2-nitro-phenylamine;
4-[4-(4-Benzyl-piperidin-1-yl)-but-1-ynyl]-benzene-1,2-diamine;
5-[4-(4-Benzyl-piperidin-1-yl)-but-1-ynyl]-1,3-dihydro-benzoimidazol-2-one;
N-{4-[4-(4-Phenylsulfanyl-piperidin-1-yl)-but-1-ynyl]-phenyl}-methanesulfonamide;
4-[3-(4-Benzyl-piperidin-1-yl)-prop-1-ynyl]-benzamide;
4-[3-(4-Benzyl-piperidin-1-yl)-prop-1-ynyl]-benzenesulfonamide;
5-[4-(4-Benzyl-piperidin-1-yl)-but-1-ynyl]-1H-indole-2,3-dione;
4-benzyl-4-hydroxy-1-(4-(3-methylphenyl)-3-butynyl) piperidine;
4-benzyl-4-hydroxy-1-(4-phenyl-3-butynyl)piperidine;
4-benzyl-4-hydroxy-1-(4-(4-aminophenyl)-3-butynyl) piperidine; and
4-(4-methylbenzyl)-4-hydroxy-1-(4-(4-aminophenyl)-3-butynyl)piperidine.

Of the above-listed exemplary compounds, the more preferred compounds are designated * and the most preferred are designated **.

The invention is also directed to a method for treating disorders responsive to the selective blockade of NMDA receptor subtypes in animals suffering thereof. Particular preferred embodiments of the 4-substituted piperidine analogs for use in the method of this invention are represented by previously defined formula (IV–VII), as well as formula (II–III) wherein Q may be selected from —CH═CH— and —C≡C— without restriction.

Exemplary preferred compounds that may be employed in the method of this invention include, without limitation:
** 1-[4-(3-Aminophenyl)-3-butynyl]-4-hydroxy-4-(4-chlorophenyl)piperidine;
1-((4-Phenyl)-3-butynyl)-4-hydroxy-4-phenylpiperidine;
* 1-[4-(3-Aminophenyl)-3-butynyl]-4-hydroxy-4-phenylpiperidine;
** 1-[4-(5-(2-Amino)pyridynyl)-3-butynyl]-4-hydroxy-4-(4-chlorophenyl)piperidine;
* 1-[4-(4-Fluorophenyl)-3-butynyl]-4-hydroxy-4-(4-chlorophenyl)piperidine;
* 1-[5-(3-Aminophenyl)-4-pentynyl]-4-hydroxy-4-(4-chlorophenyl)piperidine;
** 1-[4-(3-Aminophenyl)-3-butynyl]-4-(4-chlorophenyl)-1,2,5,6-tetrahydropyridine;
1-((4-Phenyl)-3-butynyl)-4-phenyl-1,2,5,6-tetrahydropyridine;
* 1-[4-(3-Aminophenyl)-3-butynyl]-4-phenyl-1,2,5,6-tetrahydropyridine;
** 1-[4-(5-(2-Amino)pyridynyl)-3-butynyl]-4-(4-chlorophenyl)-1,2,5,6-tetrahydropyridine;
* 1-[4-(4-Fluorophenyl)-3-butynyl]-4-(4-chlorophenyl)-1,2,5,6-tetrahydropyridine;
* 1-[5-(3-Aminophenyl)-4-pentynyl]-4-(4-chlorophenyl)-1,2,5,6-tetrahydropyridine;
* 4-Benzyl-1-[4-(3-aminophenyl)-3-butynyl]piperidine;
4-Benzyl-1-(4-phenyl-3-butynyl)piperidine;
** 4-(4-Chloro)benzyl-1-[4-(3-aminophenyl)-3-butynyl] piperidine;
** 4-(4-Chloro)benzyl-1-[4-(4-hydroxyphenyl-3-butynyl] piperidine;
** 4-(4-Chloro)benzyl-1-[4-(5-(2-amino)pyridynyl)-3-butynyl]-piperidine;
* 1-[4-(4-Fluorophenyl)-3-butynyl]-4-(3-trifluoromethylbenzyl)-piperidine;
* 4-(4-Chlorobenzyl)-1-[5-(3-aminophenyl)-4-pentynyl]-piperidine;
*4-Benzyl-1-[4-(3-aminophenyl)-3-butynyl]-3-hydroxypiperidine;
4-Benzyl-1-(4-phenyl-3-butynyl)-3-hydroxypiperidine;
** 4-(4-Chloro)benzyl-1-[4-(3-aminophenyl)-3-butynyl]3-hydroxypiperidine;
** 4-(4-chloro)benzyl-1-[4-(5-(2-amino)pyridynyl)-3-butynyl]-3-hydroxypiperidine;
* 1-[4-(4-Fluorophenyl)-3-butynyl]-4-(3-trifluoromethylbenzyl)-3-hydroxy-piperidine;
* 4-(4-Chlorobenzyl)-3-hydroxy-1-[5-(3-aminophenyl)-4-pentynyl]-piperidine;
* 1-[4-(3-Aminophenyl)-3-butynyl]-4-phenoxy-piperidine;
1-(4-Phenyl-3-butynyl)-4-phenoxypiperidine;
** 1-[4-(3-Aminophenyl)-3-butynyl]-4-(4-chloro)phenoxypiperidine;
** 1-[4-(5-(2-Amino)pyridynyl)-4-butynyl]-4-(4-chloro)phenoxypiperidine;
* 1-[4-(4-Fluorophenyl)-3-butynyl]-4-(3-trifluoromethyl)phenoxypiperidine;
* 1-[5-(3-Aminophenyl)-4-pentynyl]-4-(4-chloro)phenoxypiperidine;
* 1-[4-(3-Aminophenyl)-3-butynyl]-4-(phenyl)aminopiperidine;
1-(4-Phenyl-3-butynyl)-4-(phenyl)aminopiperidine;
** 1-[4-(3-Aminophenyl)-3-butynyl]-4-(4-chlorophenyl)aminopiperidine;
** 1-[4-(5-(2-Amino)pyridynyl)-3-butynyl]-4-(4-chlorophenyl)aminopiperidine;
* 1-[4-(4-Fluorophenyl)-3-butynyl]-4-(3-trifluoromethylphenyl)aminopiperidine;
* 4-Phenyl-1-(4-phenyl-3-butynyl)piperidine;
4-(3-(Trifluoromethyl)phenyl)-3-hydroxy-1-(4-phenyl-3-butynyl)piperidine;
* 1-(4-(4-Aminophenyl)-3-butynyl)-4-(4-chlorophenyl)-4-hydroxypiperidine;
N-n-Butyl-N'-(3-(4-(4-(4-chlorophenyl)-4-hydroxy)piperidinyl)butynyl)phenylguanidine;
** 4-Benzyl-1-(4-(3-methylphenyl)-3-butynyl)piperidine;
** 1-(4-(4-Aminophenyl)-3-butynyl)-4-benzylpiperidine;
** 4-Benzyl-4-hydroxy-1-(4-phenyl-3-butynyl)piperidine;
* 4-Benzyl-4-hydroxy-1-(4-(3-methylphenyl)-3-butynyl) piperidine;
** 1-(4-(4-Aminophenyl)-3-butynyl)-4-benzyl-4-hydroxypiperidine;
** 1-(4-(4-Aminophenyl)-3-butynyl)-4-(4-chlorobenzyl) piperidine;
** 1-(4-(4-Amino-3-fluorophenyl)-3-butynyl)-4-(4-chlorobenzyl)piperidine;
N-4-(1-(4-(3-Aminophenyl)butyn-3-yl)piperidinyl)-2-oxobenzimidazol;
** 1-(4-(2-Aminophenyl)-3-butynyl)-4-phenylpiperidine;
* 1-[5-(3-Aminophenyl)-4-pentynyl]-4-(4-chlorophenyl) aminopiperidine;

4-{4-[4-(4-Chloro-phenoxy)-piperidin-1-yl]-but-1-ynyl}-phenylamine;
N-{4-[4-(4-Phenoxy-piperidin-1-yl)-but-1-ynyl]-phenyl}-acetamide;
4-{4-[4-(4-Methyl-benzyl)-piperidin-1-yl]-but-1-ynyl}-phenylamine;
4-Benzyl-1-[4-(4-nitro-phenyl)-but-3-ynyl]-piperidine;
4-Benzyl-1-[4-(4-methoxy-phenyl)-but-3-ynyl]-piperidine;
4-[4-(4-Benzyl-piperidin-1-yl)-but-1-ynyl]-phenol;
4-Benzyl-1-[4-(4-fluoro-phenyl)-but-3-ynyl]-piperidine;
4-Benzyl-1-[4-(4-chloro-phenyl)-but-3-ynyl]-piperidine;
4-Benzyl-1-[4-(3-chloro-phenyl)-but-3-ynyl]-piperidine;
4-Benzyl-1-[4-(2,3-dichloro-phenyl)-but-3-ynyl]-piperidine;
4-Benzyl-1-[4-(3,4-dichloro-phenyl)-but-3-ynyl]-piperidine;
4-Benzyl-1-(4-p-tolyl-but-3-ynyl)-piperidine;
4-Benzyl-1-[4-(2,3-dimethyl-phenyl)-but-3-ynyl]-piperidine;
4-Benzyl-1-[4-(3,4-dimethyl-phenyl)-but-3-ynyl]-piperidine;
3-[4-(4-Benzyl-piperidin-1-yl)-but-1-ynyl]-phenylamine;
3-[4-(4-Benzyl-piperidin-1-yl)-but-1-ynyl]-benzylamine;
N-{4-[4-(4-Benzyl-piperidin-1-yl)-but-1-ynyl]-phenyl}-acetamide;
{4-[4-(4-Benzyl-piperidin-1-yl)-but-1-ynyl]-phenyl}-methyl-amine;
{4-[4-(4-Benzyl-piperidin-1-yl)-but-1-ynyl]-phenyl}-dimethyl-amine;
N-{4-[4-(4-Benzyl-piperidin-1-yl)-but-1-ynyl]-phenyl}-methanesulfonamide;
4-[4-(4-Benzyl-piperidin-1-yl)-but-1-ynyl]-benzamide;
N-(Methylsulfonyl)-N-[4-[4-[4-(phenylmethyl)-1-piperidinyl]-1-butynyl]phenyl]-methanesulfonamide;
4-[4-(4-Benzyl-piperidin-1-yl)-but-1-ynyl]-benzenesulfonamide;
4-[4-(4-Benzyl-piperidin-1-yl)-but-1-ynyl]-N-butyl-benzamide;
1-(4-Benzo[1,3]dioxol-5-yl-but-3-ynyl)-4-benzyl-piperidine;
4-Benzyl-1-[4-(2,3-dihydro-benzo[1,4]dioxin-6-yl)-but-3-ynyl]-piperidine;
4-[3-(4-Benzyl-piperidin-1-yl)-prop-1-ynyl]-phenylamine;
N-{4-[3-(4-Benzyl-piperidin-1-yl)-prop-1-ynyl]-phenyl}-methanesulfonamide;
N-{4-[4-(4-Phenylsulfanyl-piperidin-1-yl)-but-1-ynyl]-phenyl}-acetamide;
5-[4-(4-Benzyl-piperidin-1-yl)-but-1-ynyl]-1H-indole;
4-{4-[4-(4-Methyl-benzyl)-piperidin-1-yl]-but-1-ynyl}-phenol;
5-[4-(4-Benzyl-piperidin-1-yl)-but-1-ynyl]-1H-indazole;
4-[4-(4-Benzyl-piperidin-1-yl)-but-1-ynyl]-2-nitro-phenylamine;
4-[4-(4-Benzyl-piperidin-1-yl)-but-1-ynyl]-benzene-1,2-diamine;
5-[4-(4-Benzyl-piperidin-1-yl)-but-1-ynyl]-1,3-dihydro-benzoimidazol-2-one;
N-{4-[4-(4-Phenylsulfanyl-piperidin-1-yl)-but-1-ynyl]-phenyl}-methanesulfonamide;
4-[3-(4-Benzyl-piperidin-1-yl)-prop-1-ynyl]-benzamide;
4-[3-(4-Benzyl-piperidin-1-yl)-prop-1-ynyl]-benzenesulfonamide;
5-[4-(4-Benzyl-piperidin-1-yl)-but-1-ynyl]-1H-indole-2,3-dione;
4-benzyl-4-hydroxy-1-4-(3-methylphenyl)-3-butynyl)piperidine;
4-benzyl-4-hydroxy-1-(4-phenyl-3-butynyl)piperidine;
4-benzyl-4-hydroxy-1-(4-(4-aminophenyl)-3-butynyl)piperidine; and
4-(4-methylbenzyl)-4-hydroxy-1-(4-(4-aminophenyl)-3-butynyl)piperidine.

Of the above-listed exemplary compounds, the more preferred compounds for use in the method of this invention are designated * and the most preferred are designated **.

The compounds of this invention may be prepared using methods well known to those skilled in the art such as disclosed in U.S. Pat. No. 5,273,977, the disclosure of which is incorporated by reference herein, or by the novel methods of this invention. Exemplary reaction schemes I and II illustrate preparations of the compounds of this invention having alkyne functionality. The starting materials employed in Schemes I and II are readily available or can be prepared by known methods.

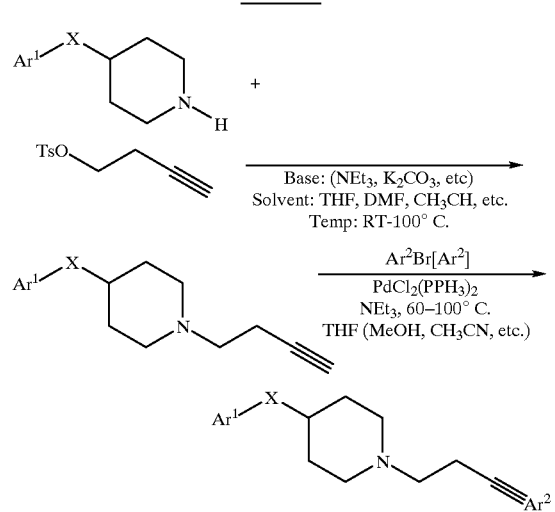

Scheme I.

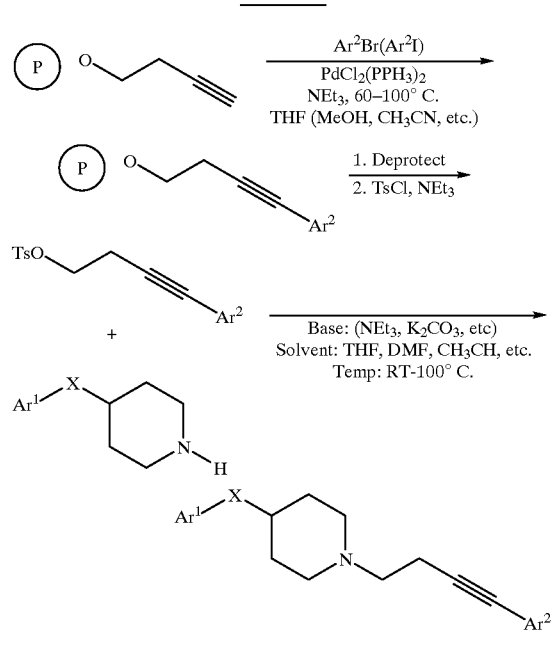

Scheme II.

The methods set forth herein, may also be employed to prepare novel intermediates of this invention. The preferred novel intermediates include:

1-(3-Butynyl)-4-hydroxy-4-phenylpiperidine;
1-(3-Butynyl)-4-hydroxy-4-((4-chloro)phenyl)piperidine;
1-(3-Butynyl)-4-hydroxy-4-((3-trifluoromethyl)phenyl) piperidine;
4-Hydroxy-4-phenyl-1-(2-propynyl)piperidine;
4-Hydroxy-1-(4-pentynyl)-4-phenylpiperidine;
1-(3-Butynyl)-4-(4-chloro)phenyl-1,2,5,6-tetrahydropyridine;
1-(3-Butynyl)-4-(4-trifluoromethyl)phenyl-1,2,5,6-tetrahydropyridine;
4-(4-Chloro)phenyl-1-(2-propynyl)-1,2,5,6-tetrahydropyridine;
4-(4-Chloro)phenyl-1-(4-pentynyl)-1,2,5,6-tetrahydropyridine;
4-Benzyl-1-(3-butynyl)piperidine;
4-(4-Chloro)benzyl-1-(3-butynyl)piperidine;
4-(3-Trifluoromethyl)benzyl-1-(3-butynyl)piperidine;
4-(4-Chloro)benzyl-1-(2-propynyl)piperidine;
4-(4-Chloro)benzyl-1-(4-pentynyl)piperidine;
4-Benzyl-1-(3-butynyl)-3-hydroxy-piperidine;
4-(4-Chloro)benzyl-1-(3-butynyl)-3-hydroxy-piperidine;
4-(3-Trifluoromethyl)benzyl-1-(3-butynyl)-3-hydroxy-piperidine;
4-(4-Chloro)benzyl-3-hydroxy-1-(2-propynyl)piperidine;
4-(4-Chloro)benzyl-3-hydroxy-1-(4-pentynyl)piperidine;
1-(3-Butynyl)-4-phenoxypiperidine;
1-(3-Butynyl)-4-(4-chloro)phenoxypiperidine;
1-(3-Butynyl)-4-(3-trifluoromethyl)phenoxypiperidine;
4-(4-Chloro)phenoxy-1-(2-propynyl)piperidine;
1-(4-Pentynyl)4-(4-chloro)phenoxypiperidine;
1-(3-Butynyl)-4-(phenyl)aminopiperidine;
1-(3-Butynyl)-4-((4-chloro)phenyl)aminopiperidine;
1-(3-Butynyl)-4-((3-trifluoromethyl)phenyl) aminopiperidine;
4-((4-Chloro)phenyl)amino-1-(2-propynyl)piperidine;
1-(But-3-ynyl)-4-(4-chlorobenzyl)piperidine;
4-Benzyl-1-(but-3-yn-1-yl)-4-hydroxypiperdine;
4-(4-Methylbenzyl)-4-hydroxy-1-(but-3-yn-1-yl)piperidine; and
1-(4-Pentynyl)4-((4-chloro)phenyl)aminopiperidine.

The compounds of the present invention are useful in treating or preventing neuronal loss, neurodegenerative diseases and chronic pain. They are also useful as anticonvulsants and for inducing anesthesia, as well as for treating epilepsy and psychosis. The therapeutic and side effect profiles of subtype-selective NMDA receptor antagonists and agonists should be markedly different from the more non-subtype-selective NMDA receptor inhibitors. The subtype-selective analogs of the present invention are expected to exhibit little or no untoward side effects caused by non-specific binding with other receptors, particularly, the PCP and glutamate bindings sites associated with the NMDA receptor. In addition, selectivity for different NMDA receptor subtypes will reduce side effects such as sedation that are common to non-subtype-selective NMDA receptor antagonists. The compounds of the present invention are effective in treating or preventing the adverse consequences of the hyperactivity of excitatory amino acids, e.g. those which are involved in the NMDA receptor system, by preventing the ligand-gated cation channels from opening and allowing excessive influx of $Ca^{++}$ into neurons, as occurs during ischemia.

Neurodegenerative diseases which may be treated with the compounds of the present invention include those selected from the group consisting of Alzheimer's disease, amyotrophic lateral sclerosis, Huntington's disease, Parkinson's disease and Down's syndrome.

The compounds of the present invention find particular utility in the treatment or prevention of neuronal loss associated with multiple strokes which give rise to dementia. After a patient has been diagnosed as suffering from a stroke, the compounds of the present invention may be administered to ameliorate the immediate ischemia and prevent further neuronal damage that may occur from recurrent strokes.

Moreover, the compounds of the present invention are able to cross the blood/brain barrier which makes them particularly useful for treating or preventing conditions involving the central nervous system.

The compounds of the invention find particular utility in treating or preventing the adverse neurological consequences of surgery. For example, coronary bypass surgery requires the use of heart-lung machines which tend to introduce air bubbles into the circulatory system which may lodge in the brain. The presence of such air bubbles robs neuronal tissue of oxygen, resulting in anoxia and ischemia. Pre- or post-surgical administration of the compounds of the present invention will treat or prevent the resulting ischemia. In a preferred embodiment, the compounds of the invention are administered to patients undergoing cardiopulmonary bypass surgery or carotid endarterectomy surgery.

The compounds of the present invention also find utility in treating or preventing chronic pain. Such chronic pain may be the result of surgery, trauma, headache, arthritis, pain from terminal cancer or degenerative diseases. The compounds of the present invention also find particular utility in the treatment of phantom pain that results from amputation of an extremity. In addition to treatment of pain, the compounds of the invention are also expected to be useful in inducing anesthesia, either general or local anesthesia, for example, during surgery.

The selective NMDA receptor subtype antagonists, agonists and modulators may be tested for in vivo anticonvulsant activity after intraperitoneal or intravenous injection using a number of anticonvulsant tests in mice (audiogenic seizure model in DBA-2 mice, pentylenetetrazol-induced seizures in mice, maximum electroshock seizure test (MES) or NMDA-induced death). The compounds may also be tested in drug discrimination tests in rats trained to discriminate PCP from saline. It is expected that most of the compounds of the present invention will not generalize to PCP at any dose. In addition, it is also expected that none of the compounds will produce a behavioral excitation in locomotor activity tests in the rodent. It is expected that such results will suggest that the selective NMDA receptor subtype antagonists and agonists of the present invention do not show the PCP-like behavioral side effects that are common to NMDA channel blockers such as MK-801 and PCP, or to competitive NMDA antagonists such as CGS 19755.

The subtype-selective NMDA receptor antagonists and agonists are also expected to show potent activity in vivo after intraperitoneal or intravenous injection suggesting that these compounds can penetrate the blood/brain barrier.

Elevated levels of glutamate has been associated with glaucoma. In addition, it has been disclosed that glaucoma management, particularly protection of retinal ganglion cells, can be achieved by administering to a patient a compound capable of reducing glutamate-induced excitotoxicity in a concentration effective to reduce the excitotoxicity. See WO94/13275. Thus, the compounds of the present invention, which are expected to cross the blood-retina barrier, are also expected to be useful in the treatment of glaucoma. Preferably, the invention is directed to the treatment of patients which have primary open-angle glaucoma, chronic closed-angle glaucoma, pseudo doexfoliation, or other types of glaucoma or ocular hypertension. Preferably, the compound is administered over an extended period (e.g. at least six months and preferably at least one year), regardless of the changes in the patient's intraocular pressure over the period of administration. The compounds of the present invention are also useful in treating CMV retinitis, particularly in combination with antiviral agents. CMV afflicts the ganglion cell layer which may result in higher levels of glutamate. Thus, NMDA receptor antagonists could block retinitis by blocking the toxicity effect of high levels of glutamate.

Aminoglycoside antibiotics have been used successfully in the treatment of serious Gram-negative bacterial infections. However, prolonged treatment with these antibiotics will result in the destruction of sensory hearing cells of the inner ear and consequently, induce permanent loss of hearing. A recent study of Basile, et al. (Nature Medicine, 2: 1338–1344, 1996) indicated that aminoglycosides produce a polyamine-like enhancement of glutamate excitotoxicity through their interaction with the NMDA receptor. Thus, compounds of the present invention with NMDA receptor antagonist activity will be useful in preventing aminoglycoside antibiotics-induced hearing loss by antagonizing their interaction with the receptor.

The compounds of the present invention are useful in treating headaches, in particular, migraine headaches. During migraine attack, a sensory disturbance with unique changes of brain blood flow will result in the development of characteristic migraine auras. Since this unique phenomena has been replicated in animal experiments with cortical-spreading depression (CSD) of Leaõ, A. A. P. J., Neurophysiol. 7:359–390 (1944), CSD is considered an important phenomena in the pathophysiology of migraine with aura (Tepley et al., In: Biomagnetism, eds. S. Williamson, L. Kaufmann, pp. 327–330, Plenum Press, New York (1990)). The CSD is associated with the propagation (2~6 mm/s) of transient changes in electrical activity which relate to the failure of ion homoestatis in the brain, efflux of excitatory amino acids from the neurons and increased energy metabolism (Lauritzen, M., Acta Neurol. Scand. 76 (Suppl. 113) :4–40 (1987)). It has been demonstrated that the initiation of CSD in a variety of animals, including humans, involved the release of glutamate and could be triggered by NMDA (Curtis et al., Nature 191:1010–1011 (1961); and Lauritzen et al., Brain Res. 475:317–327 (1988)). Subtype selective NMDA antagonists will be therapeutically useful for migraine headache because of their expected low side effects, their ability to cross the blood brain barrier and their systemic bioavailability.

Bladder activity is controlled by parasympathetic preganglionic neurons in the sacral spinal cord (DeGroat et al., J. Auton. Nerv. Sys. 3:135–160(1981)). In humans, it has been shown that the highest density of NMDA receptors in the spinal cord are located at the sacral level, including those areas that putatively contain bladder parasympathetic preganglionic neurons (Shaw et al., Brain Research 539:164–168 (1991)). Because NMDA receptors are excitatory in nature, pharmacological blockade of these receptors would suppress bladder activity. It has been shown that the noncompetitive NMDA receptor antagonist MK801 increased the frequency of micturition in rat (Vera and Nadelhaft, Neuroscience Letters 134:135–138(1991)). In addition, competitive NMDA receptor antagonists have also been shown to produce a dose-dependent inhibition of bladder and of urethral sphincter activity (U.S. Pat. No. 5,192,751). Thus, it is anticipated that subtype-selective NMDA receptor antagonists will be effective in the treatment of urinary incontinence mediated by their modulation on the receptor channel activity.

Non-competitive NMDA receptor antagonist MK801 has been shown to be effective in a variety of animal models of anxiety which are highly predictive of human anxiety (Clineschmidt, B. V. et al., Drug Dev. Res. 2:147–163 (1982)). In addition, NMDA receptor glycine site antagonists are shown to be effective in the rat potentiated startle test (Anthony, E. W., Eur. J. Pharmacol. 250:317–324 (1993)) as well as several other animal anxiolytic models (Winslow, J. et al, Eur. J. Pharmacol. 190:11–22 (1990); Dunn, R. et al., Eur. J. Pharmacol. 214:207–214 (1992); and Kehne, J. H. et al, Eur. J. Pharmacol. 193:282–292 (1981)).

Glycine site antagonists, (+) HA-966 and 5,7-dichlorokynurenic acid were found to selectively antagonize d-amphetamine induced stimulation when injected into rat nucleus accumbens but not in striatum (Hutson, P. H. et al., Br. J. Pharmacol. 103:2037–2044 (1991)). Interestingly, (+) HA-966 was also found to block PCP and MK801-induced behavioral arousal (Bristow, L. J. et al., Br. J. Pharmacol. 108:1156–1163 (1993)). These findings suggest that a potential use of NMDA receptor channel modulators, but not channel blockers, as atypical neuroleptics.

It has been shown that in an animal model of Parkinson's disease—MPP$^+$ or methamphetamine-induced damage to dopaminergic neurons—can be inhibited by NMDA receptor antagonists (Rojas et al., Drug Dev. Res. 29:222–226 (1993); and Sonsalla et al, Science 243;398–400 (1989)). In addition, NMDA receptor antagonists have been shown to inhibit haloperidol-induced catalepsy (Schmidt, W. J. et al., Amino Acids 1:225–237 (1991)), increase activity in rodents depleted of monoamines (Carlsson et al., Trends Neurosci. 13:272–276 (1990)) and increase ipsilateral rotation after unilateral substantia nigra lesion in rats (Snell, L. D. et al., J. Pharmacol. Exp. Ther. 235:50–57 (1985)). These are also experimental animal models of Parkinson's disease. In animal studies, the antiparkinsonian agent amantadine and memantine showed antiparkinsonian-like activity in animals at plasma levels leading to NMDA receptor antagonism (Danysz, W. et al., J. Neural Trans. 7:155–166, (1994)). Thus, it is possible that these antiparkinsonian agents act therapeutically through antagonism of an NMDA receptor. Therefore, the balance of NMDA receptor activity maybe important for the regulation of extrapyramidal function relating to the appearance of parkinsonian symptoms.

It is well known to use opiates, e.g., morphine, in the medical field to alleviate pain. (As used herein, the term "opiates" is intended to mean any preparation or derivative of opium, especially the alkaloids naturally contained therein, of which there are about twenty, e.g., morphine, noscapine, codeine, papaverine, and thebaine, and their derivatives.) Unfortunately, with continued use, the body builds up a tolerance for the opiate, and, thus, for continued relief, the patient must be subjected to progressively larger doses. Tolerance develops after both acute and chronic morphine administration (Kornetsky et al., Science 162:1011–1012 (1968); Way et al., J. Pharmacol. Exp Ther. 167:1–8 (1969); Huidobro et al., J. Pharmacol. Exp Ther. 198:318–329 (1976); Lutfy et al., J. Pharmacol. Exp Ther. 256:575–580 (1991)). This, in itself, can be detrimental to the patient's health. Furthermore, a time can come when the tolerance is substantially complete and the pain killing properties of the drug are no longer effective. Additionally, administration of higher doses of morphine may lead to respiratory depression, causing the patient to stop breathing. Seeking alternative drugs to produce analgesia without development of tolerance or as an adjunct therapy to block tolerance without interference with analgesia is an active area of research.

Recent studies have suggested a modulatory role for the NMDA receptor in morphine tolerance. (Trujillo et al., Science 251:85–87 (1991); Marek et al., Brain Res. 547:77–81 (1991); Tiseo et al., J. Pharmacol. Exp Ther. 264:1090–1096 (1993); Lutfy et al., Brain Res. 616:83–88 (1993); Herman et al., Neuropsychopharmacology 12:269–294 (1995).) Further, it has been reported that NMDA receptor antagonists are useful for inhibiting opioid tolerance and some of the symptoms of opioid withdrawal. Thus, the present invention is also directed to the administration of the compounds described herein to inhibit opiate tolerance and to treat or ameliorate the symptoms of opiate withdrawal by blocking the glycine co-agonist site associated with the NMDA receptor.

Thus, the present invention is directed to compounds having high affinity to a particular NMDA receptor subunit (subtype) and low affinity to other sites such as dopamine and other catecholamine receptors. According to the present invention, those compounds having high binding to a particular NMDA subunit exhibit an $IC_{50}$ of about 100 $\mu$M or less in an NMDA subunit binding assay (see Table 1). Preferably, the compounds of the present invention exhibit a selective subunit $IC_{50}$ of 10 $\mu$M or less. More preferably, the compounds of the present invention exhibit a selective subunit $IC_{50}$ of about 1.0 $\mu$M or less, more preferably about 0.1 $\mu$M or less.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for anxiety disorders, e.g., generalized anxiety disorder, phobic disorders, obsessional compulsive disorder, panic disorder and post traumatic stress disorders or for schizophrenia or other psychoses. Preferably, about 0.01 to about 10 mg/kg is orally administered to treat or prevent such disorders. For intramuscular injection, the dose is generally about one-half of the oral dose. For example, for treatment or prevention of anxiety, a suitable intramuscular dose would be about 0.0025 to about 15 mg/kg, and most preferably, from about 0.01 to about 10 mg/kg.

In the method of treatment or prevention of neuronal loss in ischemia, brain and spinal cord trauma, hypoxia, hypoglycemia, and surgery, to treat or prevent glaucoma or urinary incontinence, as well as for the treatment of Alzheimer's disease, amyotrophic lateral sclerosis, Huntington's disease, Parkinson's disease and Down's Syndrome, or in a method of treating a disease in which the pathophysiology of the disorder involves hyperactivity of the excitatory amino acids or NMDA receptor-ion channel related neurotoxicity, the pharmaceutical compositions of the invention may comprise the compounds of the present invention at a unit dose level of about 0.01 to about 50 mg/kg of body weight, or an equivalent amount of the pharmaceutically acceptable salt thereof, on a regimen of 1–4 times per day. When used to treat chronic pain, migraine headache, to induce anesthesia, to treat or prevent opiate tolerance or to treat opiate withdrawal, the compounds of the invention may be administered at a unit dosage level of from about 0.01 to about 50 mg/kg of body weight, or an equivalent amount of the pharmaceutically acceptable salt thereof, on a regimen of 1–4 times per day. Of course, it is understood that the exact treatment level will depend upon the case history of the animal, e.g., human being, that is treated. The precise treatment level can be determined by one of ordinary skill in the art without undue experimentation.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular subtype-selective NMDA receptor antagonist or agonist of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, and the like.

The pharmaceutical compositions of the invention may be administered to any animal which may experience the beneficial effects of the compounds of the invention. Foremost among such animals are mammals, e.g., humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries include, without limitation, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetyl-cellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension include, for example, sodium carboxymethyl cellulose, sorbitol, and/or dextran. Optionally, the suspension may also contain stabilizers.

The characterization of NMDA subunit binding sites in vitro has been difficult because of the lack of selective drug ligands. Thus, the compounds of the present invention may be used to characterize the NMDA subunits and their distribution. Particularly preferred selective NMDA receptor subtype antagonists and agonists of the present invention which may be used for this purpose are isotopically radiolabelled derivatives, e.g., where one or more of the atoms are replaced with $^{3}H$, $^{11}C$, $^{14}C$, $^{15}N$, or $^{18}F$.

Electrophysiological Assays at NMDA Receptor Subunits

Preparation of RNA. cDNA clones encoding the NR1A, NR2A, NR2B, NR2C and NR2D rat NMDA receptor subtypes were provided by Dr. P. H. Seeburg (see, Moriyoshi et al., *Nature* (Lond.) 354:31–37 (1991); Kutsuwada et al., *Nature* (Lond.) 358:36–41 (1992) Monyer et al., *Science* (Washington. D.C.) 256:1217–1221 (1992); Ikeda et al., *FEBS Lett.* 313:34–38 (1992); Ishii et al., *J. Biol. Chem.* 268:2836–2843 (1993) for details of these clones or their mouse homologs). The clones were transformed into appropriate host bacteria and plasmid preparations were made with conventional DNA purification techniques. A sample of each clone was linearized by restriction enzyme digestion and cRNA was synthesized with T3 RNA polymerase. The cRNA was diluted to 400 ng/$\mu$l and stored in 1 $\mu$l aliquots at —80° C. until injection.

The Xenopus oocyte expression system. Mature female *Xenopus laevis* were anaesthetized (20–40 min) using 0.15% 3-aminobenzoic acid ethyl ester (MS-222) and 2–4 ovarian lobes were surgically removed. Oocytes at developmental stages IV–VI (Dumont, J. N., *J. Morphol.* 136:153–180 (1972)), were dissected from the ovary still surrounded by enveloping ovarian tissues. Follicle-enclosed oocytes were micro-injected with 1:1 mixtures of cRNA:NR1A+NR2A, 2B, 2C or 2D; injecting ~2, 5, or 20 ng of RNA encoding each receptor subunit. NR1A encoding cRNA was injected alone at ~20 ng. Oocytes were stored in Barth's medium containing (in mM):NaCl, 88; KCl, 1; CaCl$_2$, 0.41; Ca(NO$_3$)$_2$, 0.33; MgSO$_4$, 0.82 NaHCO$_3$, 2.4; HEPES 5, pH 7.4, with 0.1 mg/ml gentamicin sulphate. While oocytes were still surrounded by enveloping ovarian tissues the Barth's medium was supplemented with 0.1% bovine serum. Oocytes were defolliculated 1–2 days following injections by treatment with collagenase (0.5 mg/ml Sigma Type I for 0.5–1 hr) (Miledi and Woodward, *J. Physiol.* (Lond.) 416:601–621 (1989)) and subsequently stored in serum-free medium.

Electrical recordings were made using a conventional two-electrode voltage clamp (Dagan TEV-200) over periods ranging between 3–21 days following injection. (Woodward et al., *Mol. Pharmacol.* 41: 89–103 (1992)). Oocytes were placed in a 0.1 ml recording chamber continuously perfused (5–15 ml min$^{-1}$) with frog Ringer's solution containing (in mM):NaCl, 115; KCl, 2; CaCl$_2$, 1.8; HEPES, 5; pH 7.4. Drugs were applied by bath perfusion. Using oocytes expressing different subunit combinations of NMDA receptor, NMDA currents were activated by co-application of glutamate (100 $\mu$M) and glycine (1–100 $\mu$M). Inhibitory potency of the novel antagonists was assessed on responses elicited by fixed concentrations of glutamate and glycine, by measuring reductions in current induced by progressively increasing concentrations of antagonist. Concentration-inhibition curves were fit with equation 1.

$$I/I_{control}=1/(1+([antagonist]/10^{-pIC50})^n) \qquad \text{Eq. 1}$$

in which $I_{control}$ is the current evoked by agonists alone, $pIC_{50}$=−log $IC_{50}$, $IC_{50}$ is the concentration of antagonist that produces half maximal inhibition, and n is the slope factor. (De Lean et al., *Am. J. Physiol.* 235:E97–102 (1978)). For incomplete curves analysis by fitting was unreliable and IC$_{50}$ values were calculated by simple regression over linear portions of the curves (Origin: Microcal Software).

Maximal Electroshock-induced Seizures. Seizures were induced by application of current (50 mA, 60 pulses/sec, 0.8 sec pulse width, 1 sec duration, d.c.) through saline-coated corneal electrodes using a Ugo Basile ECT device (Model 7801). Mice were restrained by gripping the loose skin on their dorsal surface, electrodes were held lightly against the two cornea, then current was applied and mice were observed for a period of up to 30 sec for the occurrence of a tonic hindlimb extensor response. A tonic seizure was defined as a hindlimb extension in excess of 90 degrees from the plane of the body. Results were treated in a quantal manner.

The examples which follow are intended as an illustration of certain preferred embodiments of the invention, and no limitation of the invention is implied.

EXAMPLE 1

1-(3-Butynyl)-4-(4-chlorobenzyl)piperidine

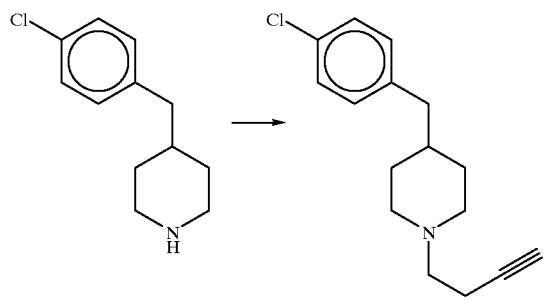

A suspension of NaHCO$_3$ (4 g) and 4-[(4-chlorophenyl) methyl]piperidine (18 mmol) in dimethylformamide (DMF) (25 mL) is stirred under a N$_2$ atm at 0° C., and treated dropwise with 3-butynyltosylate (20 mmol) as a solution in DMF (50 mL). The reaction mixture is heated at 80° C. and stirred an additional 18 hours. After cooling the reaction mixture is stirred vigorously with the addition of water (200 mL), and then extracted with ethyl acetate. The organic layer is dried over magnesium sulfate, filtered and evaporated. The residue is purified by silica gel column chromatography (100:1 CH$_2$Cl$_2$:MeOH) to give 1-(3-butynyl)-4-(4-chlorophenyl)piperidine.

EXAMPLE 2

1-(3-Butynyl)-4-[(4-trifluoromethylphenyl)methyl] piperidine

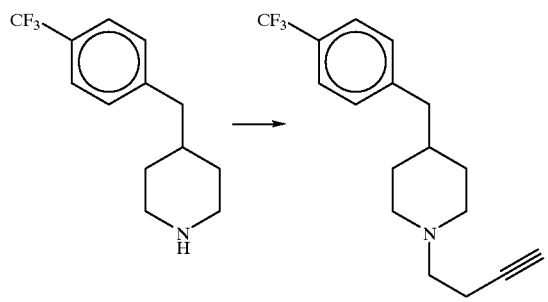

A mixture of 4-[(4-trifluoromethylphenyl)methyl] piperidine (30 mmol), K$_2$CO$_3$ (4.5 g) and 3-butynyltosylate (39 mmol) in acetonitrile (150 mL) is heated to reflux for 8 hr. After cooling, the acetonitrile is removed on a rotary evaporator and the residue partitioned between dichloromethane and water. The combined organic solution is dried over sodium sulfate, filtered and evaporated. The product is purified by silica gel column chromatography.

Alternatively, the reagents are mixed in an identical manner except that acetone is used as a solvent, and the mixture is heated at reflux for 16 hr. After cooling, the reaction mixture is filtered and the filtrate evaporated. The residue is purified by silica gel chromatography.

EXAMPLE 3

4-(4-Chloro)benzyl-1-[4-(3-aminophenyl)-3-butynyl]-piperidine

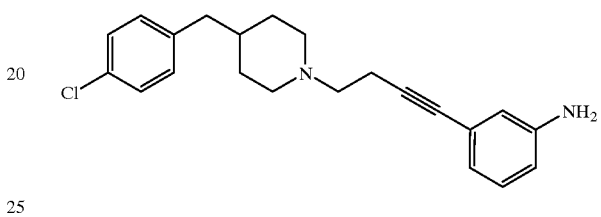

A mixture of 1-(3-butynyl)-4-[(4-chlorophenyl)methyl] piperidine (3.8 mmol), which is prepared according to Example 1, and m-bromoaniline (3.8 mmol) in n-butylamine (20 mL) under a nitrogen atmosphere is treated with tetrakis (triphenylphosphine)palladium (0) (0.17 g) and then heated to reflux for 18 hr. After removing the solvent in vacuo, the residue is dissolved in CH2Cl$_2$ and washed with saturated NaHCO$_3$. The combined organic solution is dried over magnesium sulfate, filtered and evaporated. The above described product is purified by silica gel chromatography.

Alternatively, a suspension of NaHCO$_3$(1 g) and 4-[(4-chlorophenyl)methyl]piperidine (4 mmol) in DMF (25 mL) is stirred under a N$_2$ atm at 0° C. and treated dropwise with 1-[(4-methylphenyl)sulfonyl]oxy-4-(3-amino)phenyl-3-butyne (4 mmol), which is prepared according to Example 5, as a solution in DMF (20 mL). The reaction mixture is heated to 80° C. for 12 hr. After cooling, the reaction mixture is stirred vigorously with the addition of water (200 mL) and then extracted with ethyl acetate. The organic layer is dried over magnesium sulfate, filtered and evaporated. The residue is purified by silica gel column chromatography (100:1 CH$_2$Cl$_2$:MeOH) to give the above described product.

EXAMPLE 4

4-(4-Trifluoromethyl)benzyl-1-[4-(3-aminophenyl)-3-butynyl]-piperidine

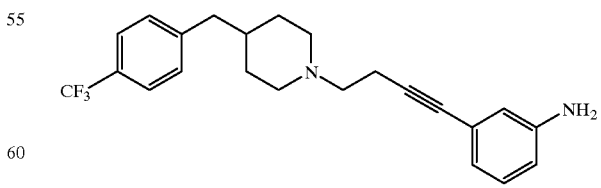

A mixture of 1-(3-butynyl)-4-[(4-(trifluoromethyl) phenyl)methyl]piperidine (4 mmol), which is prepared according to Example 2, m-iodoaniline (4 mmol) and triethylamine (5 mL) in acetonitrile (50 mL) under a nitrogen atmosphere is treated with bis(triphenylphosphine) palladium (II) chloride (0.5 g). After refluxing for 16 hr, the solvent is removed by rotary evaporation and the above described product purified by silica gel chromatography (100:1 $CH_2Cl_2$:MeOH).

EXAMPLE 5

1-(t-Butyldimethylsiloxy)-4-(3-amino-phenyl)-3-butyne

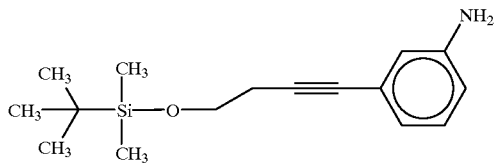

A mixture of 1-(t-butyldimethylsilyloxy)-3-butyne (10 mmol) and m-bromoaniline (10 mmol) in n-butylamine (50 mL) under a nitrogen atmosphere is treated with tetrakis (triphenylphosphine)palladium (0) (0.17 g) and then heated to reflux for 18 hr. After removing the solvent in vacuo, the residue is dissolved in $CH_2Cl_2$ and washed with saturated $NaHCO_3$. The combined organic solution is dried over magnesium sulfate, filtered and evaporated to give the above described silyl protected adduct.

EXAMPLE 6

1-tosyl-4-(3-aminophenyl)-3-butyne

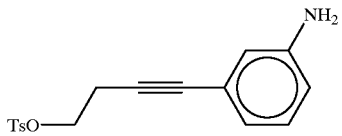

A solution of 1-(t-butyldimethylsilyloxy)4-(3-aminophenyl-3-butyne (3 mmol), which is prepared according to Example 5, in $CH_2Cl_2$ (100 mL) is cooled in an ice bath and then treated with tetrabutylammonium fluoride (3.1 mmol). After stirring for 30 min, 100 mL water is added, the organic layer partitioned and dried over magnesium sulfate, filtered and evaporated. The residue is dissolved in THF (50 mL) with triethylamine (2 mL) and then treated with tosyl chloride (3 mmol). After stirring at room temperature for 4 hr, saturated aqueous NaCl (100 mL) is added and the organic phase partitioned. The aqueous layer is back extracted with methylene chloride. The combined organic layers are dried over magnesium sulfate, filtered and evaporated. The above described tosylated product is purified by column chromatography and may be used in a manner similar to that described for Example 2 to prepare 4-substituted piperidine analogs of this invention.

EXAMPLE 7

1-[4-(5-(2-Amino)pyridynyl)-3-butynyl]-4-hydroxy-4-(4-chlorophenyl)piperidine

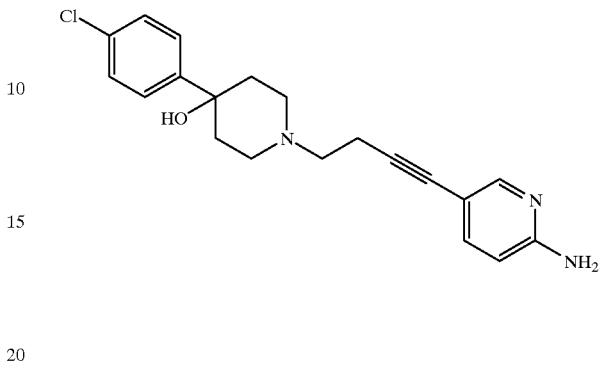

The above described product is prepared in a manner similar to that described for Examples 3 or 4.

EXAMPLE 8

1-[4-(3-Aminophenyl)-3-butynyl]-4-hydroxy-4-(4-chlorophenyl)piperidine

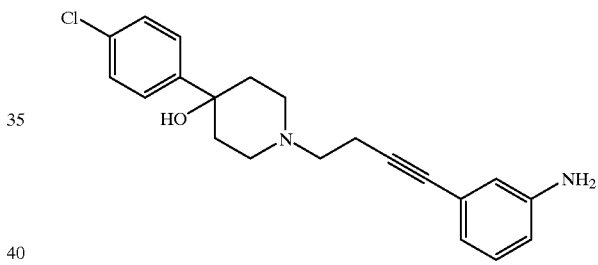

A) 1-(3-Butynyl)-4-(4-chlorophenyl)-4-hydroxypiperidine. A mixture of 1-mesylbut-3-yne (1.48 g, 10.0 mmol), 4-(4-chlorophenyl)-4-hydroxypiperidine (2.54 g, 12.0 mmol) and $K_2CO_3$ (4.14 g, 30.0 mmol) in $CH_3CN$ (25 mL) is refluxed for 12 hr. The mixture is filtered and washed with EtOAc (3×30 mL). The filtrate is evaporated in vacuo and is purified by flash chromatography to give the product as a colorless solid (2.30 g, 87%): mp 98–100° C.; $^1H$ NMR ($CDCl_3$) 1.55 (s, 1 H), 1.74 (m, 2 H), 1.99 (m, 1 H), 2.10 (m, 2 H), 2.42 (m, 4 H), 2.65 (m, 2 H), 2.79 (m, 2 H), 7.32 (d, J=7.2 Hz, 2 H) , 7.42 (d, J=7.2 Hz, 2 H).
B)1-(4-(3-Aminophenyl)-3-butynyl)-4-(4-chlorophenyl)-4-hydroxypiperidine. A solution of 1-(3-butynyl)-4-(4-chlorophenyl)-4-hydroxypiperidine (263 mg, 1.00 mmol), 3-iodoaniline (208 mg, 0.950 mmol) and tetrakis (triphenylphosphine) palladium (0) (46 mg) in n-butylamine (5 mL) is allowed to reflux for 15 hr. The solvent is evaporated in vacuo to give a residue, which is purified by flash chromatography giving the product as an off white solid (231 mg, 69%): mp 139–140° C.; $^1H$ NMR ($CDCl_3$) 1.71 (m, 3 H), 2.12 (m, 2 H), 2.56 (m, 4 H), 2.73 (m, 2 H), 2.84 (m, 2 H), 3.60 (bs, 2 H), 6.59 (d, J=7.5 Hz, 1 H), 6.72 (s, 1 H), 6.79 (d, J=7.5 Hz, 1 H), 7.07 (dd, $J_1=J_2$=7.5 Hz, 1 H), 7.33 (d, J=9.7 Hz, 2 H), 7.46 (d, J=9.7 Hz, 2 H).

EXAMPLE 9

1-[4-(3-Aminophenyl)-3-butynyl]-4-(4-chlorophenyl)-1,2,5,6-tetrahydropyridine

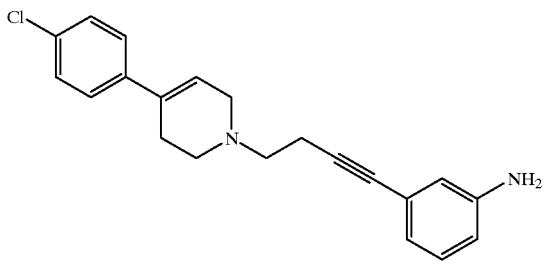

The above described product is prepared in a manner similar to that described for Examples 3 or 4.

EXAMPLE 10

1-[4-(5-(2-Amino)pyridynyl)-3-butynyl]-4-(4-chlorophenyl)-1,2,5,6-tetrahydropyridine

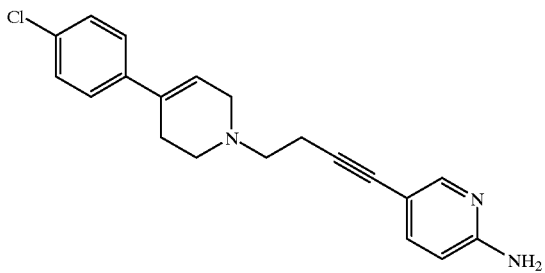

The above described product is prepared in a manner similar to that described for Examples 3 or 4.

EXAMPLE 11

1-[4-(3-Aminophenyl)-3-butynyl]-4-phenyl-1,2,5,6-tetrahydropyridine

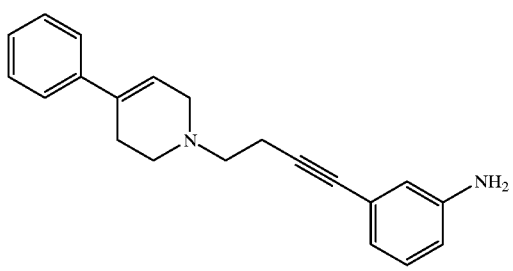

The above described product is prepared in a manner similar to that described for Examples 3 or 4.

EXAMPLE 12

1-[4-(4-Methylaminophenyl)-3-butynyl]-4-phenyl-1,2,5,6-tetrahydropyridine

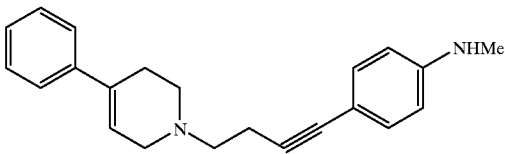

The above described product is prepared in a manner similar to that described for Examples 3 or 4.

EXAMPLE 13

1-[4-(4-Aminophenyl)-3-butynyl]-4-phenyl-1,2,5,6-tetrahydropyridine

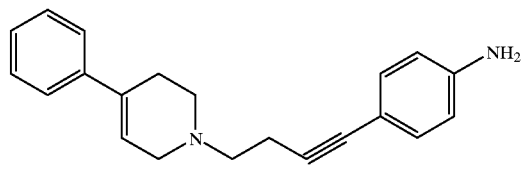

The above described product is prepared in a manner similar to that described for Examples 3 or 4.

EXAMPLE 14

1-[4-(5-Aminophenyl)-3-butynyl]-4-phenyl-1,2,5,6-tetrahydropyridine

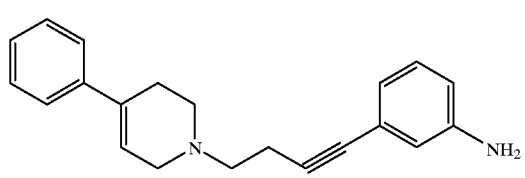

The above described product is prepared in a manner similar to that described for Examples 3 or 4.

EXAMPLE 15

1-[4-(5-Methylaminophenyl)-3-butynyl]-4-phenyl-1,2,5,6-tetrahydropyridine

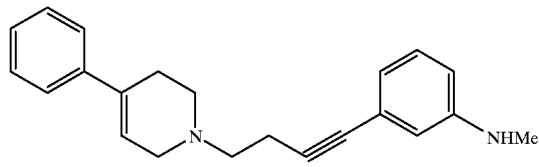

The above described product is prepared in a manner similar to that described for Examples 3 or 4.

EXAMPLE 16

1-[4-(4-Methoxyaminophenyl)-3-butynyl]-4-phenyl-1,2,5,6-tetrahydropyridine

The above described product is prepared in a manner similar to that described for Examples 3 or 4.

EXAMPLE 17

4-(4-Chloro)benzyl-1-[4-(5-(2-amino)pyridynyl)-3-butynyl]-piperidine

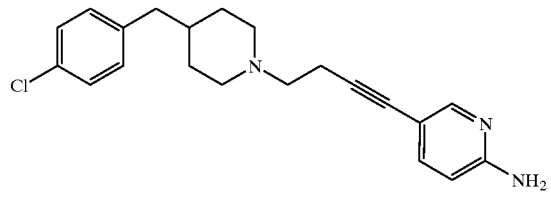

The above described product is prepared in a manner similar to that described for Examples 3 or 4.

EXAMPLE 18

4-Benzyl-1-(4-phenyl-3-butynyl)piperidine

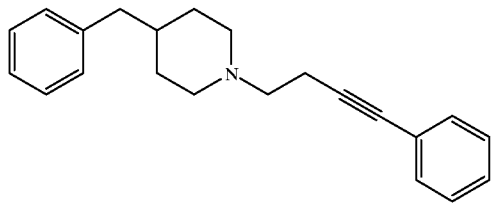

A mixture of 1-mesyl-4-phenylbut-3-yne (200 mg, 0.87 mmol), 4-benzylpiperidine (175 mg, 1.00 mmol) and $K_2CO_3$ (368 mg, 2.67 mmol) in $CH_3CN$ (10 mL) is refluxed for 12 hr. The mixture is filtered and washed with EtOAc (3×15 mL). The filtrate is evaporated in vacuo and is purified by flash chromatography to give the product as an oil (100 mg, 38%): $^1$H NMR (CDCl$_3$) 1.45 (m, 2 H), 1.52 (m, 1 H), 1.65 (m, 2 H), 2.05 (t, J=6.6 Hz, 2 H), 2.54 (m, 2 H), 2.68 (m, 4 H), 2.97 (d, J=11 Hz, 2 H), 7.13–7.36 (m, 10 H).

EXAMPLE 19

4-(4-Chloro)benzyl-1-[4-(3-aminophenyl)-3-butynyl]-3-hydroxypiperidine

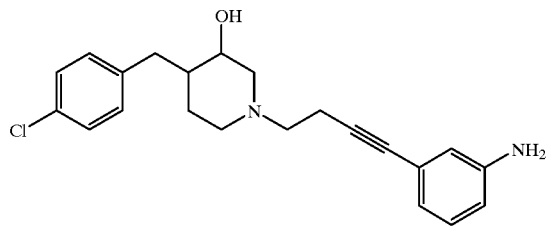

The above described product is prepared in a manner similar to that described for Examples 3 or 4.

EXAMPLE 20

4-(4-Chloro)benzyl-1-[4-(5-(2-amino)-pyridynyl)-3-butynyl]-3-hydroxypiperidine

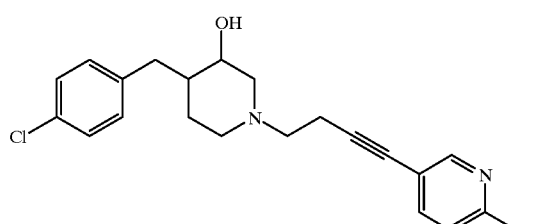

The above described product is prepared in a manner similar to that described for Examples 3 or 4.

EXAMPLE 21

1-[4-(3-Aminophenyl)-3-butynyl]-4-(4-chloro)phenoxypiperidine

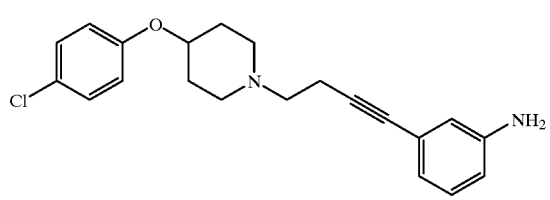

The above described product is prepared in a manner similar to that described for Examples 3 or 4.

EXAMPLE 22

1-[4-(5-(2-Amino)pyridynyl)-3-butynyl]-4-(4-chloro)phenoxypiperidine

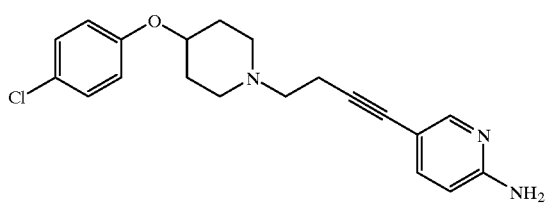

The above described product is prepared in a manner similar to that described for Examples 3 or 4.

EXAMPLE 23

1-[4-(3-Aminophenyl)-3-butynyl]-4-(4-chlorophenyl)aminopiperidine

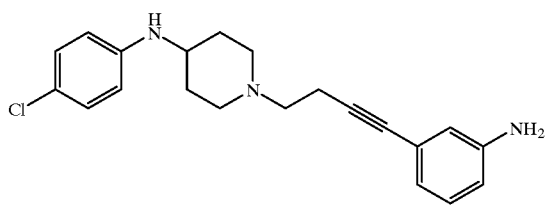

The above described product is prepared in a manner similar to that described for Examples 3 and 4.

EXAMPLE 24

1-[4-(5-(2-Amino)pyridynyl)-3-butynyl]-4-(4-chlorophenyl)aminopiperidine

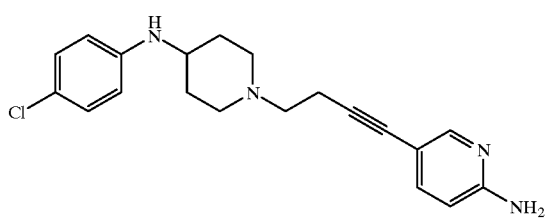

The above described product is prepared in a manner similar to that described for Examples 3 or 4.

EXAMPLE 25

4-Phenyl-1-(4-phenyl-3-butynyl)piperidine

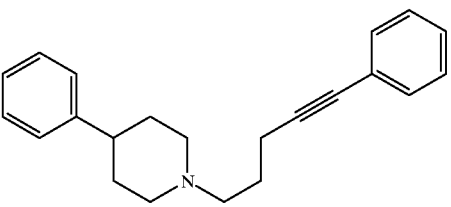

A) 1-Mesylbut-3-yne. Methanesulfonyl chloride (45.8 g, 400 mmol) is added to a stirred solution of 3-butyn-1-ol (14.0 g, 200 mmol) in dry $CH_2Cl_2$ (120 mL) containing 148 mL of pyridine. The resulting solution is allowed to stir at room temperature for 20 hr. The mixture is poured onto ice (50 g). The organic layer is separated and the water phase is extracted with $CH_2Cl_2$ (3×30 ml). The combined organic extract is evaporated to remove most of the pyridine. $CH_2Cl_2$ (100 mL) is added to the residue. The resulting solution is washed with 100 mL of 0.5 N HCl solution, 50 mL of cold saturated $NaHCO_3$ solution and 30 mL of brine and then is dried over $Na_2SO_4$. Evaporation of $CH_2Cl_2$ gives the product (22 g, 75%) $^1$H NMR (CDCl$_3$) 2.06 (t, J=2.7 Hz, 1 H), 2.66 (dt, $J_1$=2.7 Hz, $J_2$=6.6 Hz, 2 H), 4.30 (t, J=6.6 Hz, 2 H).

B) 1-Mesyl-4-phenylbut-3-yne. A mixture of 1-mesylbut-3-yne (758 mg, 5.10 mmol), iodobenzene (1.25 g, 6.00 mmol), copper(I) iodide (40 mg), PdCl$_2$(PPh$_3$)$_2$ (70 mg) in 12 mL of Et$_3$N is stirred under N$_2$ for 20 hr. The mixture is filtered and washed with Et$_3$N (3×15 mL). The filtrate is evaporated in vacuo and is purified by flash chromatography to give the product as a pale yellow oil (560 mg, 50%) $^1$H NMR (CDCl$_3$) 2.91 (t, J=6.6 Hz, 2 H), 4.39 (t, J=6.6 Hz, 2 H), 7.30 (m, 3 H), 7.38 (m, 2 H).

C) 4-Phenyl-1-(4-phenyl-3-butynyl)piperidine. A mixture of 1-mesyl-4-phenylbut-3-yne (200 mg, 0.870 mmol), 4-phenylpiperidine (120 mg, 0.744 mmol) and K$_2$CO$_3$ (308 mg, 2.23 mmol) in 10 mL of CH$_3$CN is refluxed for 12 hr. The mixture is filtered and washed with EtOAc (3×15 mL). The filtrate is evaporated in vacuo and is purified by flash chromatography to give the product (104 mg, 41%): mp 65–66° C.; $^1$H NMR (CDCl$_3$) 1.81 (m, 4 H), 2.26 (m, 2 H), 2.65 (m, 1 H), 2.69 (m, 2 H), 2.76 (m, 2 H), 3.13 (d, J=11 Hz, 2 H), 7.13–7.36 (m, 10 H).

EXAMPLE 26

4-(3-(Trifluoromethyl)phenyl)-3-hydroxy-1-(4-phenyl-3-butynyl)piperidine

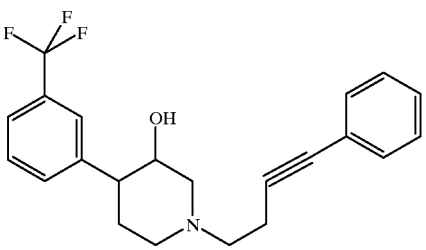

A mixture of 1-mesyl-4-phenylbut-3-yne (352 mg, 1.57 mmol), 4-(3-( trifluoromethyl)phenyl)piperidin-3-ol hydrochloride (530 mg, 1.88 mmol) and K₂CO₃ (542 mg, 3.93 mmol) in 20 mL of CH₃CN is refluxed for 12 hr. The mixture is filtered and washed with EtOAc (3×20 mL). The filtrate is evaporated in vacuo and is purified by flash chromatography to give the product as an off white solid (120 mg, 21%): mp 77–79° C.; ¹H NMR (CDCl₃) 1.71 (m, 2 H), 2.15 (m, 3 H), 2.40 (bs, 1 H), 2.62 (m, 4 H), 2.72 (m, 1 H), 2.83 (m, 2 H), 7.27–7.81 (m, 9 H).

EXAMPLE 27

1-(4-(4-Aminophenyl)-3-butynyl)-4-(4-chlorophenyl)-4-hydroxypiperidine

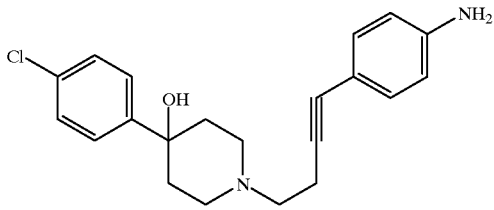

A solution of 1-(3-butynyl)-4-(4-chlorophenyl)-4-hydroxypiperidine (263 mg, 1.00 mmol), 4-iodoaniline (208 mg, 0.950 mmol) and 50 mg of tetrakis(triphenylphosphine) palladium in 10 mL of butylamine is allowed to reflux for 20 hr. The solvent is evaporated in vacuo to give a residue, which is purified by flash chromatography giving the product as an off white solid (70 mg, 21%): mp 134–136βC; ¹H NMR (CDCl₃) 1.59 (m, 2 H), 1.90 (m, 2 H), 2.47 (m, 6 H), 2.67 (m, 2 H), 3.59 (s, 1 H), 3.87 (bs, 2 H), 6.46 (d, J=8.1 Hz, 1 H), 7.02 (d, J=8.1 Hz, 2 H), 7.14 (d, J=8.4 Hz, 2 H), 7.33 (d, J=8.4 Hz, 2 H).

EXAMPLE 28

N-n-Butyl-N'-(3-(4-(4-(4-chlorophenyl)-4-hydroxy)piperidinyl)butynyl)phenylguanidine

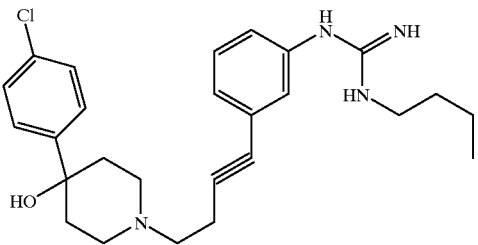

A) 3-Iodophenylcyanamide. To a solution of 3-iodoaniline (3.50 g, 16.0 mmol) in 50 mL of ether is added cyanogen bromide (1.79 g, 16.9 mmol) at 0° C. The resulting mixture is allowed to stir at rt for 12 hr. The solid is collected by filtration and dried in vacuo to give the product as a solid (3.32 g, 85%): mp 86–88° C. (EtOH/H₂O); ¹H NMR (DMSO-d₆) 6.93 (d, J=8.1 Hz, 1 H), 7.08 (dd, J₁=7.5 Hz, J₂=8.1 Hz, 1 H), 7.23 (s, 1 H), 7.34 (d, J=7.5 Hz, 1 H).

B) N-n-Butyl-N'-(3-(4-(4-(4-chlorophenyl)-4-hydroxy)piperidinyl)butynyl)phenylguanidine. A mixture of 1-(3-butynyl)-4-(4-chlorophenyl)-4-hydroxypiperidine (132 mg, 0.500 mmol), 3-iodophenylcyanamide (146 mg, 0.600 mmol), Pd(PPh₃)₄ (25 mg, 0.020 mmol) in 5 mL of n-butylamine is allowed to reflux for 12 hr. Evaporation of solvent gives a residue, which is purified by flash chroma-tography giving the product as a solid (90 mg, 40%): βmp 98–100° C.; ¹H NMR (CDCl₃) 0.93 (m, 5 H), 1.34 (m, 4 H), 1.48 (m, 3 H), 1.71 (m, 3 H), 2.12 (m, 2 H), 2.56 (m, 3 H), 2.76 (m, 1 H), 2.84 (m, 1 H), 3.12 (m, 2 H), 3.75 (bs, 1 H), 6.75–7.46 (m, 8 H). Anal. Calcd for C₂₆H₃₃ClN₄O: C, 68.93; H, 7.34; N, 12.37. Found: C, 69.30; H, 7.57; N, 12.00.

EXAMPLE 29

4-Benzyl-1-(4-(3-methylphenyl)-3-butynyl)piperidine

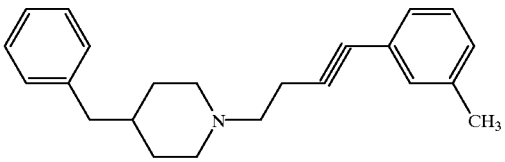

A) 1-Mesyl-4-(3-methylphenyl)but-3-yne. A mixture of 1-mesylbut-3-yne (758 mg, 5.10 mmol), 3-iodotoluene (1.31 g, 6.00 mmol), copper (I) iodide (40 mg), PdCl₂(PPh₃)₂ (70 mg) in 12 mL of Et₃N is stirred at room temperature under N₂ for 20 hr. The mixture is filtered and washed with Et₃N (3×15 mL). The filtrate is evaporated in vacuo and is purified by flash chromatography to give the product as a pale yellow oil (565 mg, 47%): ¹H NMR (CDCl₃) 2.31 (s, 3 H), 2.88 (t, J=6.9 Hz, 2 H), 3.07 (s, 3 H), 4.38 (t, J=6.9 Hz, 2 H), 7.20 (m, 4 H).

B) 4-Benzyl-1-(4-(3-methylphenyl)-3-butynyl) piperidine. A mixture of 1-mesyl-4-(3-methylphenyl)but-3-yne (214 mg, 0.900 mmol), 4-benzylpiperidine (189 mg, 1.08 mmol) and K₂CO₃ (370 mg, 2.67 mmol) in 10 mL of CH₃CN is refluxed for 12 hr. The mixture is filtered and washed with EtOAc (3×15 mL). The filtrate is evaporated in vacuo and is purified by flash chromatography to give the product as an oil (90 mg, 31%): ¹H NMR (CDCl₃) 1.40 (m, 2 H), 1.51 (m, 1 H), 1.65 (m, 2 H), 2.05 (t, J=6.6 Hz, 2 H), 2.31 (s, 3 H), 2.54 (m, 2 H), 2.68 (m, 4 H), 2.97 (d, J=11.4 Hz, 2 H), 7.13–7.28 (m, 9 H).

EXAMPLE 30

1-(4-(4-Aminophenyl)-3-butynyl)-4-benzylpiperidine

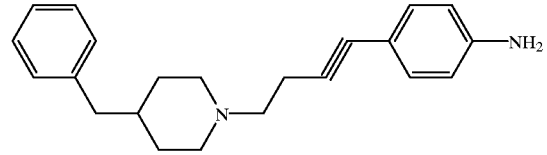

A) 1-(3-Butynyl)-4-benzylpiperidine. A mixture of 1-mesylbut-3-yne (3.03 g, 20.0 mmol), 4-benzylpiperidine (4.21 g, 24.0 mmol) and K₂CO₃ (8.28 g, 60.0 mmol) in 50 mL of CH₃CN is refluxed for 12 hr. The mixture is filtered and washed with EtOAc (3×30 mL). The filtrate is evaporated in vacuo and is purified by flash chromatography to give the product as pale yellow oil (4.30 g, 95%): ¹H NMR (CDCl₃) 1.32 (m, 2 H), 1.51 (m, 1 H), 1.65 (m, 2 H), 1.94 (m, 3 H), 2.36 (m, 2 H), 2.54 (m, 4 H), 2.86 (d, J=11.4 Hz, 2 H), 7.12–7.27 (m, 5 H).

B) 1-(4-(4-Aminophenyl)-3-butynyl)-4-benzylpiperidine. A mixture of 1-(but-3-yn-1-yl)-4-benzylpiperidine (227 mg, 1.00 mmol), 4-iodoaniline (263 mg, 1.20 mmol), copper (I) iodide (15 mg), PdCl$_2$(PPh$_3$)$_2$ (28 mg) in 10 mL of Et$_3$N is stirred at room temperature under N$_2$ for 20 hr. The mixture is filtered and washed with Et$_3$N (3×15 mL). The filtrate is evaporated in vacuo and is purified by flash chromatography to give the product as a pale yellow oil (50 mg, 16%) $^1$H NMR (CDCl$_3$) 1.29 (m, 2 H), 1.51 (m, 1 H), 1.66 (m, 2 H), 1.99 (m, 2 H), 2.58 (m, 6 H), 2.91 (m, 2 H), 3.73 (m, 2 H), 6.55 (d, J=7.8 Hz, 2 H), 7.13–7.28 (m, 7 H).

EXAMPLE 31

4-Benzyl-4-hydroxy-1-(4-phenyl-3-butynyl) piperidine

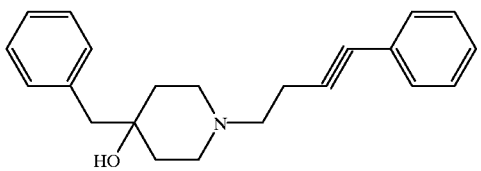

A mixture of 1-mesyl-4-phenylbut-3-yne (300 mg, 1.34 mmol), 4-benzyl-4-hydroxypiperidine (307 mg, 1.61 mmol) and K$_2$CO$_3$ (555 mg, 4.02 mmol) in 15 mL of CH$_3$CN is refluxed for 12 hr. The mixture is filtered and washed with EtOAc (3×20 mL). The filtrate is evaporated in vacuo and is purified by flash chromatography to give the product as an off-white solid (130 mg, 30%): mp 80–82° C.; $^1$H NMR (CDCl$_3$) 1.50 (m, 3 H), 1.74 (m, 2 H), 2.41 (m, 2 H), 2.58 (m, 3 H), 2.75 (m, 5 H), 7.11–7.38 (m, 10 H).

EXAMPLE 32

4-Benzyl-4-hydroxy-1-(4-(3-methylphenyl)-3-butynyl)piperidine

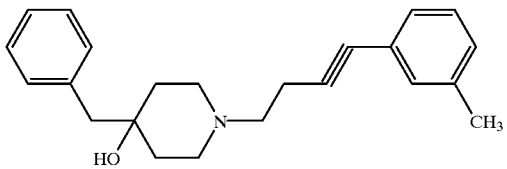

A mixture of 1-mesyl-4-(3-methylphenyl)but-3-yne (344 mg, 1.45 mmol), 4-benzyl-4-hydroxy-piperidine (332 mg, 1.73 mmol) and K$_2$CO$_3$ (598 mg, 4.34 mmol) in 15 mL of CH$_3$CN is refluxed for 12 hr. The mixture is filtered and washed with EtOAc (3×20 mL). The filtrate is evaporated in vacuo and is purified by flash chromatography to give the product as a brown oil (100 mg, 20%) $^1$H NMR (CDCl$_3$) 1.37 (s, 1 H) , 1.55 (m, 2 H) 1.75 (m, 2 H), 2.30 (s, 3 H), 2.41 (m, 2 H), 2.60 (m, 3 H), 2.75 (m, 5 H), 7.11–7.31 (m, 9 H)

EXAMPLE 33

1-(4-(4-Aminophenyl)-3-butynyl)-4-benzyl-4-hydroxypiperidine

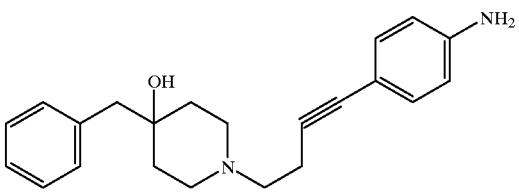

A) 4-Benzyl-1-(3-butynyl)-4-hydroxypiperidine. A mixture of 1-mesylbut-3-yne (1.63 g, 11.0 mmol), 4-benzyl-4-hydroxypiperidine (1.91 g, 10.0 mmol) and K$_2$CO$_3$ (4.14 g, 30.0 mmol) in 50 mL of CH$_3$CN is refluxed for 12 hr. The mixture is filtered and washed with EtOAc (3×30 mL). The filtrate is evaporated in vacuo and is purified by flash chromatography to give the product as a colorless solid (2.1 g, 86%): mp 51–53° C.; $^1$H NMR (CDCl$_3$) 1.50 (m, 2 H), 1.65 (m, 3 H), 1.97 (s, 1 H), 2.35 (m, 4 H), 2.62 (m, 4 H), 2.75 (s, 1 H), 7.21–7.31 (m, 5 H).

B) 1-(4-(4-Aminophenyl)but-3-yn-1-yl)-4-benzyl-4-hydroxypiperidine. A mixture of 4-benzyl-1-(but-3-yn-1-yl)-4-hydroxypiperidine (243 mg, 1.00 mmol), 4-iodoaniline (219 mg, 1.00 mmol), copper(I) iodide (40 mg), PdCl$_2$(PPh$_3$)$_2$ (50 mg, 0.04 mmol) in 10 mL of Et$_3$N is stirred at room temperature under N$_2$ for 20 hr. The mixture is filtered and washed with Et$_3$N (3×15 mL). The filtrate is evaporated in vacuo and is purified by flash chromatography to give the product as a brown oil (100 mg, 30%): $^1$H NMR (CDCl3) 1.49 (m, 3 H), 1.72 (m, 2 H), 2.38 (m, 2 H), 2.55–2.66 (m, 6 H), 2.74 (s, 2 H), 3.75 (s, 2 H), 6.52 (d, J=8.4 Hz, 2 H), 7.15–7.30 (m, 7 H).

EXAMPLE 34

1-(4-(4-Aminophenyl)-3-butynyl)-4-(4-chlorobenzyl)piperidine

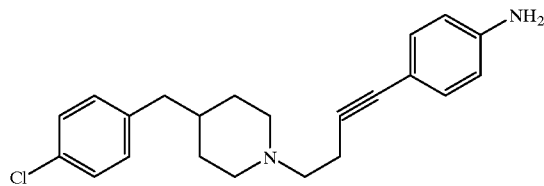

A) 4-(4-Chlorobenzyl)-1-(3-butynyl)piperidine. A mixture of 1-mesylbut-3-yne (2.22 g, 15.0 mmol), 4-(4-chlorobenzyl)piperidine hydrochloride (2.95 g, 12.0 mmol), K$_2$CO$_3$ (4.97 g, 36.0 mmol) in 50 mL of CH$_3$CN is allowed to reflux for 12 hr. The inorganic salt is removed through a short column of silica gel and washed with EtOAc (3×30 mL). Evaporation of solvents gives a residue, which is purified by flash chromatography giving the product as pale yellow oil (2.67 g, 85%): $^1$H NMR (CDCl$_3$) 1.31 (m, 2 H), 1.50 (m, 1 H), 1.59 (m, 2 H), 1.96 (m, 3 H), 2.38 (m, 2 H), 2.48 (m, 2 H), 2.55 (m, 2 H), 2.88 (d, J=11.1 Hz, 2 H), 7.04 (d, J=8.1 Hz, 2 H), 7.26 (d, J=8.1 Hz, 2 H).

B) 1-(4-(4-Aminophenyl)-3-butynyl)-4-(4-chlorobenzyl) piperidine. To a solution of 4-(4-chlorobenzyl)-1-(but-3-yn-1-yl)piperidine (318 mg, 1.21 mmol) and 4-iodoaniline (265 mg, 2.19 mmol) in 10 mL of butylamine is added 70 mg of Pd(PPh$_3$)$_4$. The resulting solution is allowed to reflux for 24 hr. The solvent is evaporated in vacua and the residue is purified by flash chromatography giving the title product as a brown oil (50 mg, 12%): $^1$H NMR (CDCl$_3$) 1.24 (m, 2 H), 1.44 (m, 1 H), 1.58 (m, 2 H), 1.96 (m, 3 H), 2.15 (m, 2 H), 2.55 (m, 4 H), 2.89 (m, 2 H), 3.75 (bs, 2 H), 6.53 (d, J=6.0 Hz, 2 H), 7.05 (m, 2 H), 7.20 (m, 4 H).

EXAMPLE 35

1-(4-(4-Amino-3-fluorophenyl)-3-butynyl)-4-(4-chlorobenzyl)piperidine

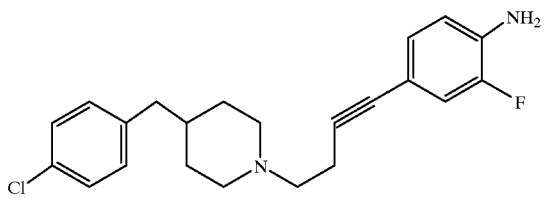

To a solution of 4-(4-chlorobenzyl)-1-(but-3-yn-1-yl) piperidine (400 mg, 1.53 mmol) and 2-fluoro-4-iodoaniline (436 mg, 1.84 mmol) in 10 mL of butylamine is added 70 mg of Pd(PPh$_3$)$_4$. The resulting solution is allowed to reflux for 24 hr. The solvent is evaporated in vacuo and the residue is purified by flash chromatography giving the title product as a brown oil (100 mg, 18%): $^1$H NMR (CDCl$_3$) 1.25 (m, 2 H), 1.46 (m, 1 H), 1.58 (m, 2 H), 1.97 (m, 2 H), 2.56 (m, 6 H), 2.88 (m, 2 H), 3.83 (bs, 2 H), 6.62 (m, 1 H), 6.80–7.24 (m, 6 H).

EXAMPLE 36

4-Benzyl-1-(butynyl)-4-hydroxypiperidine

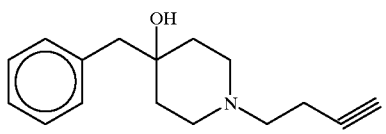

A mixture of 1-mesylbut-3-yne (1.63 g, 11.0 mmol), 4-benyzl-4-hydroxypiperdine (1.91 g, 10.0 mmol) and K$_2$CO$_3$ (4.14 g, 30.0 mmol) in 50 mL of CH$_3$CN is refluxed for 12 hr. The mixture is filtered and is washed with EtOAc (3×30 mL). The filtrate is evaporated in vacuo and is purified by flash chromatography to give the product as a colorless solid (2.1 g, 86%): mp 51–53° C.; $^1$H NMR (CDCl$_3$) 1.50 (m, 2 H), 1.65 (m, 3 H), 1.97 (s, 1 H), 2.35 (m, 4 H), 2.62 (m, 4 H), 2.75 (s, 1 H), 7.21–7.31 (m, 5 H).

EXAMPLE 37

4-{4-[4-(4-Chloro-phenoxy)-piperidin-1-yl]-but-1-ynyl}-phenylamine

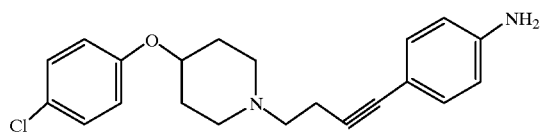

The above described product is prepared in a manner similar to that described for Examples 3 or 4.

EXAMPLE 38

N-{4-[4-(4-Phenoxy-piperidin-1-yl)-but-1-ynyl]-phenyl}-acetamide

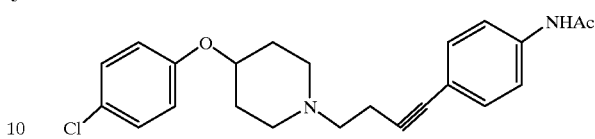

The above described product is prepared in a manner similar to that described for Examples 3 or 4.

EXAMPLE 39

4-{4-[4-(4-Methyl-benzyl)-piperidin-1-yl]-but-1-ynyl}-phenylamine

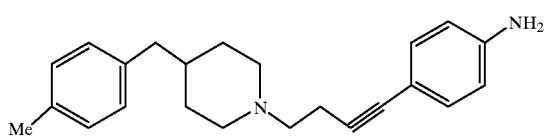

The above described product is prepared in a manner similar to that described for Examples 3 or 4.

EXAMPLE 40

4-Benzyl-1-[4-(4-nitro-phenyl)-but-3-ynyl]-piperidine

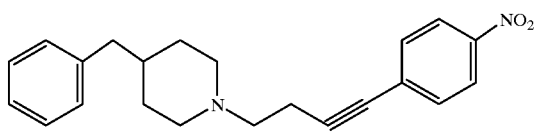

The above described product is prepared in a manner similar to that described for Examples 3 or 4.

EXAMPLE 41

4-Benzyl-1-[4-(4-methoxy-phenyl)-but-3-ynyl]-piperidine

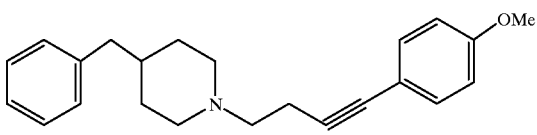

A mixture of 4-benzyl-1-(but-3-yn-1-yl)piperidine (455 mg, 2 mmol), 4-iodoanisole (702 mg, 3 mmol) and tetrakis (triphenylphosphine)palladium (0) (116 mg, 0.1 mmol) is stirred in pyrrolidine (5 mL) and deoxygenated by bubbling nitrogen through the solution. The mixture is stirred at room temperature under nitrogen for 20 hr. The pyrrolidine is evaporated and the residue purified by medium pressure liquid chromatography on silica gel eluting with 25% to 75% ethyl acetate in hexane to give the product as a colorless oil (286 mg, 43%). The oil is stirred in ethanol (10 mL) and oxalic acid dihydrate (108 mg) in ethanol (2 mL) added. The mixture is allowed to stand in the freezer overnight. The salt crystallizes; it is collected, washed with cold ethanol and dried at 50° C. under high vacuum to give the title compound as an off-white solid (290 mg): mp 158–161° C.

EXAMPLE 42

4-[4-(4-Benzyl-piperidin-1-yl)-but-1-ynyl]-phenol

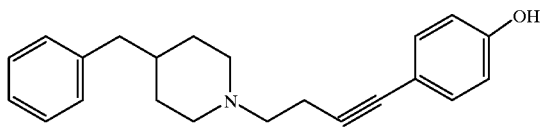

The above described product is prepared in a manner similar to that described for Example 41.

EXAMPLE 43

4-Benzyl-1-[4-(4-fluoro-phenyl)-but-3-ynyl]-piperidine

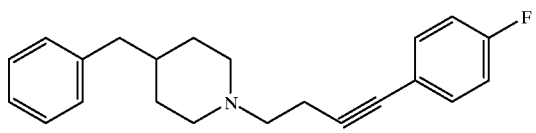

The above described product is prepared in a manner similar to that described for Example 41.

EXAMPLE 44

4-Benzyl-1-[4-(4-chloro-phenyl)-but-3-ynyl]-piperidine

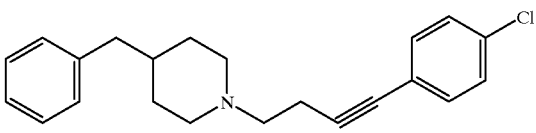

The above described product is prepared in a manner similar to that described for Example 41.

EXAMPLE 45

4-Benzyl-1-[4-(3-chloro-phenyl)-but-3-ynyl]-piperidine

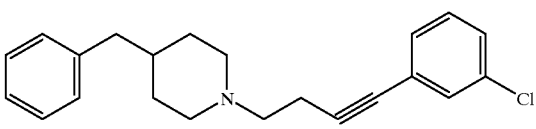

The above described product is prepared in a manner similar to that described for Example 41.

EXAMPLE 46

4-Benzyl-1-[4-(2,3-dichloro-phenyl)-but-3-ynyl]-piperidine

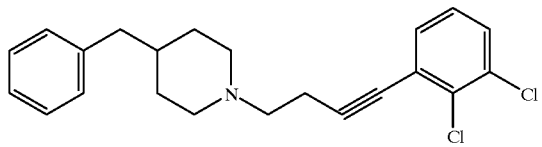

The above described product is prepared in a manner similar to that described for Example 41.

EXAMPLE 47

4-Benzyl-1-[4-(3,4-dichloro-phenyl)-but-3-ynyl]-piperidine

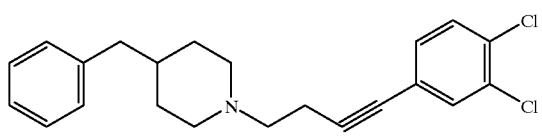

The above described product is prepared in a manner similar to that described for Example 41.

EXAMPLE 48

4-Benzyl-1-(4-p-tolyl-but-3-ynyl)-piperidine

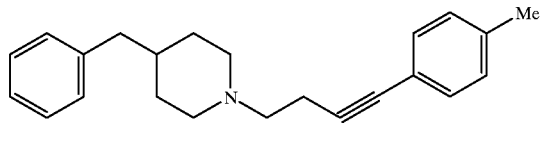

The above described product is prepared in a manner similar to that described for Example 41.

EXAMPLE 49

4-Benzyl-1-[4-(2,3-dimethyl-phenyl)-but-3-ynyl]-piperidine

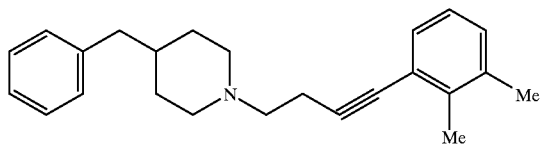

The above described product is prepared in a manner similar to that described for Example 41.

EXAMPLE 50

4-Benzyl-1-[4-(3,4-dimethyl-phenyl)-but-3-ynyl]-piperidine

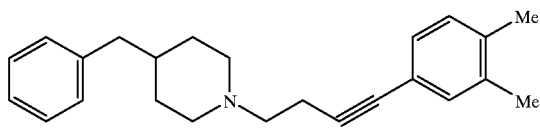

The above described product is prepared in a manner similar to that described for Example 41.

EXAMPLE 51

3-[4-(4-Benzyl-piperidin-1-yl)-but-1-ynyl]-phenylamine

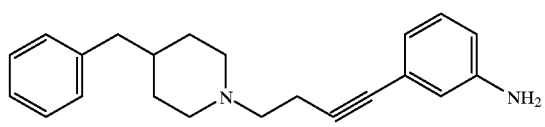

The above described product is prepared in a manner similar to that described for Example 41.

EXAMPLE 52

3-[4-(4-Benzyl-piperidin-1-yl)-but-1-ynyl]-benzylamine

The above described product is prepared in a manner similar to that described for Example 41.

EXAMPLE 53

N-{4-[4-(4-Benzyl-piperidin-1-yl)-but-1-ynyl]-phenyl}-acetamide

The above described product is prepared in a manner similar to that described for Example 41.

EXAMPLE 54

{4-[4-(4-Benzyl-piperidin-1-yl)-but-1-ynyl]-phenyl}-methyl-amine

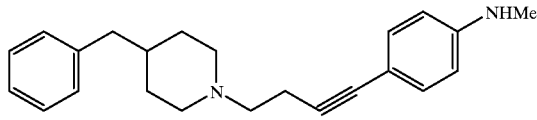

The above described product is prepared in a manner similar to that described for Example 41.

EXAMPLE 55

{4-[4-(4-Benzyl-piperidin-1-yl)-but-1-ynyl]-phenyl}-dimethyl-amine

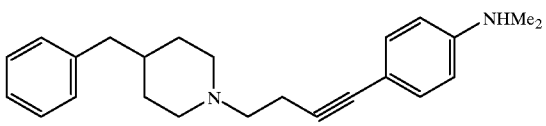

The above described product is prepared in a manner similar to that described for Example 41.

EXAMPLE 56

N-{4-[4-(4-Benzyl-piperidin-1-yl)-but-1-ynyl]-phenyl}-methanesulfonamide

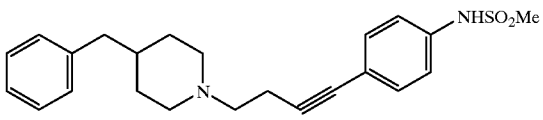

The above described product is prepared in a manner similar to that described for Example 41.

EXAMPLE 57

4-[4-(4-Benzyl-piperidin-1-yl)-but-1-ynyl]-benzamide

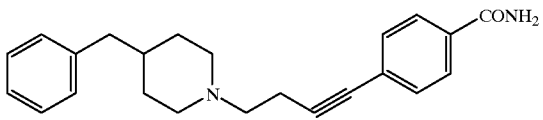

The above described product is prepared in a manner similar to that described for Example 41.

EXAMPLE 58

N-(Methylsulfonyl)-N-[4-[4-[4-(phenylmethyl)-1-piperidinyl]-1-butynyl]phenyl]-methanesulfonamide

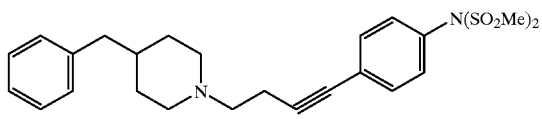

The above described product is prepared in a manner similar to that described for Example 41.

EXAMPLE 59

4-[4-(4-Benzyl-piperidin-1-yl)-but-1-ynyl]-benzenesulfonamide

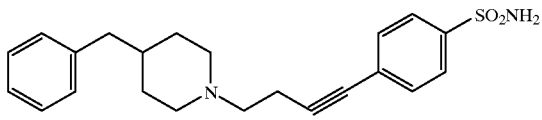

The above described product is prepared in a manner similar to that described for Example 41.

EXAMPLE 60

4-[4-(4-Benzyl-piperidin-1-yl)-but-1-ynyl]-N-butyl-benzamide

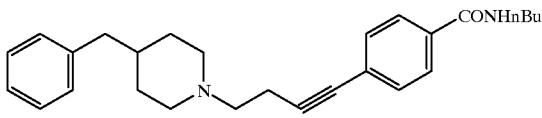

The above described product is prepared in a manner similar to that described for Example 41.

EXAMPLE 61

1-(4-Benzo[1,3]dioxol-5-yl-but-3-ynyl)-4-benzyl-piperidine

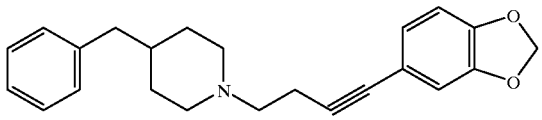

The above described product is prepared in a manner similar to that described for Example 41.

EXAMPLE 62

4-Benzyl-1-[4-(2,3-dihydro-benzo[1,4]dioxin-6-yl)-but-3-ynyl]-piperidine

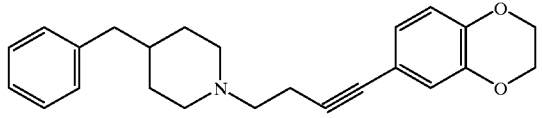

The above described product is prepared in a manner similar to that described for Example 41.

EXAMPLE 63

4-[3-(4-Benzyl-piperidin-1-yl)-prop-1-ynyl]-phenylamine

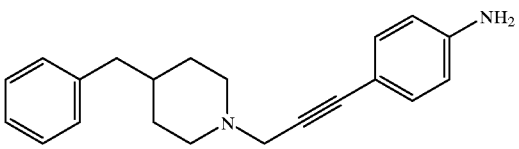

The above described product is prepared in a manner similar to that described for Example 41.

EXAMPLE 64

N-{4-[3-(4-Benzyl-piperidin-1-yl)-prop-1-ynyl]-phenyl}-methanesulfonamide

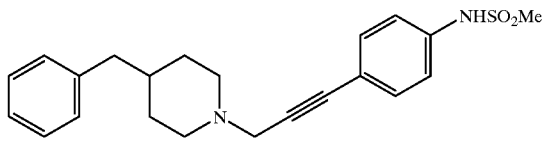

The above described product is prepared in a manner similar to that described for Example 41.

EXAMPLE 65

N-{4-[4-(4-Phenylsulfanyl-piperidin-1-yl)-but-1-ynyl]-phenyl}-acetamide

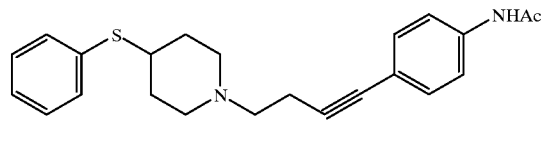

The above described product is prepared in a manner similar to that described for Example 41.

EXAMPLE 66

5-[4-(4-Benzyl-piperidin-1-yl)-but-1-ynyl]-1H-indole

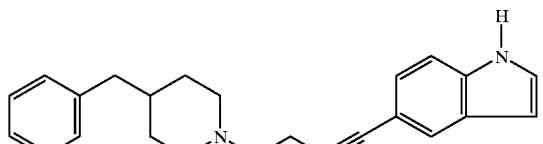

A) 1-Benzenesulfonyl-5-bromoindole. A mixture of 5-bromoindole (5 g, 25.5 mmol) and tetra-n-butylammonium hydrogen sulfate (866 mg, 2.55 mmol) in 50% NaOH (50 mL) and toluene (200 mL) is stirred at room temperature for 5 min. Benzenesulfonyl chloride (3.57 mL, 28 mmol) is added and the mixture stirred for 1 hr. The mixture is diluted with water (500 mL) and extracted with EtOAc (3×100 mL). The extracts are washed with brine (250 mL), dried over $MgSO_4$, filtered and evaporated to a yellow oil. The oil is purified by medium-pressure column chromatography on silica gel eluting with 10% EtOAc/hexanes to give the title compound as a white solid (7.81 g).

B) 1-Benzenesulfonyl-5-[4-(4-benzyl-piperidin-1-yl)-but-1-ynyl]-1H-indole. A mixture of 1-benzenesulfonyl-5-bromoindole (1.34 g, 4 mmol), 4-benzyl-1-(3-butynyl)-piperidine (908 mg, 4 mmol) and tetrakis(triphenylphosphine)palladium (0) (600 mg) is stirred in pyrrolidine (50 mL) at 50° C. under $N_2$ overnight. Most of the pyrrolidine is evaporated and the residue purified by medium-pressure column chromatography on silica gel eluting with 50% increasing to 100% EtOAc/hexanes to give the title compound as a pale yellow oil (1.55 g).

C) 5-[4-(4-Benzyl-piperidin-1-yl)-but-1-ynyl]-1H-indole. A mixture of 1-benzenesulfonyl-5-[4-(4-benzyl-piperidin-1-yl)-but-1-ynyl]-1H-indole (1.49 g, 3.1 mmol) is stirred in EtOH (200 mL) and 50% NaOH (1 mL) at room temperature for 3 days. Most of the EtOH is evaporated and the residue diluted with water (200 mL). The precipitate is filtered off and washed copiously with water. The precipitate is recrystallized from hot EtOH to give the title compound as an off-white solid (854 mg): mp 165–166° C.

EXAMPLE 67

4-{4-[4-(4-Methyl-benzyl)-piperidin-1-yl]-but-1-ynyl}-phenol

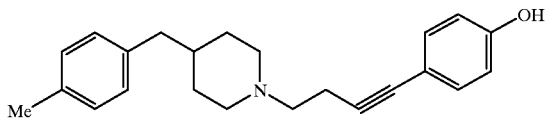

A) 4-(4-Methylbenzyl)-1-(1-butyn-3-yl)piperidine. A mixture of 4-methylbenzylpiperidine hydrochloride (1.129 g, 5.0 mmol), 1-butyn-3-ylmethanesulfonate (0.888 g, 5.0 mmol), and potassium carbonate (2.48 g, 12.5 mmol) in 30 mL of acetonitrile is heated to reflux for 12 hr. The inorganic salt is removed through a short column of silica gel and washed with ethyl acetate (3×30 mL). Evaporation of solvents gives a residue, which is purified by flash chromatography (50% EtOAc in hexane), giving 0.96 g (80%) of the title compound as pale yellow oil. $^1$H NMR (CDCl$_3$) 1.26 (m, 3 H), 1.50 (m, 1 H), 1.61 (m, 2 H), 1.96 (m, 2 H), 2.31 (s, 3 H), 2.36 (m, 2 H), 2.47–2.59 (m, 4 H), 2.86 (d, J=11.4 Hz, 2 H), 7.07 (dd, J1==7.8 Hz, J2=10.5 Hz, 4 H).

B) 4-{4-[4-(4-Methyl-benzyl)-piperidin-1-yl]-but-1-ynyl}-phenol. To a solution of 4-(4-methylbenzyl)-1-(1-butyn-3-yl)piperidine (400 mg, 1.66 mmol) and 4-iodophenol (347 mg, 1.57 mmol) in 10 mL of butylamine is added 80 mg of Pd(PPh$_3$)$_4$. The resulting solution is allowed to stir at 55° C. for 24 hr. The solvent is evaporated in vacuo and the residue is purified by flash chromatography (20% EtOAc in hexane) to give 150 mg (27%) of the title product as a brown oil. $^1$H NMR (CDCl$_3$) 1.34 (m, 2 H), 1.50 (m, 1 H), 1.65 (d, J=11.7 Hz, 2 H), 2.08 (t, J=12.0 Hz, 2 H), 2.33 (s, 3 H), 2.47 (d, J=6.9 Hz, 2 H), 2.60 (t, J=7.2 Hz, 2 H), 2.68 (t, J=7.5 Hz, 2 H), 3.02 (d, J=11.1 Hz, 2 H), 3.49 (brs, 1 H), 6.68 (d, J=8.1 Hz, 2 H), 7.01 (d, J=7.5 Hz, 2 H), 7.08 (d, J=7.5 Hz, 2 H), 7.20 (d, J=8.1 Hz, 2 H).

EXAMPLE 68

5-[4-(4-Benzyl-piperidin-1-yl)-but-1-ynyl]-1H-indazole

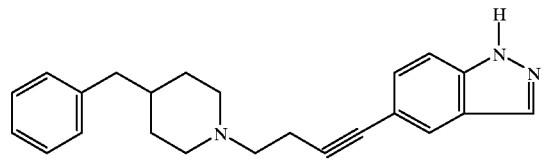

The above described product is prepared in a manner similar to that described for Example 41.

EXAMPLE 69

4-[4-(4-Benzyl-piperidin-1-yl)-but-1-ynyl]-2-nitro-phenylamine

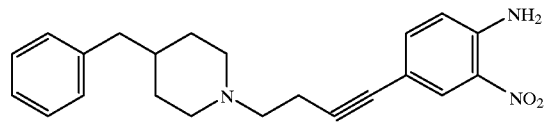

A mixture of 4-benzyl-1-(3-butynyl)piperidine (2.27 g, 10 mmol), 4-bromo-2-nitroaniline (2.17 g, 10 mmol) and tetrakis(triphenylphosphine)palladium (0) (600 mg) is stirred in pyrrolidine (50 mL) at 50° C. under $N_2$ overnight. Most of the pyrrolidine is evaporated and the residue purified by medium-pressure column chromatography on silica gel eluting with 40% increasing to 60% EtOAc/hexanes to give a red oil (3.14 g). A portion of this oil (340 mg) is dissolved in EtOH (8 mL) and oxalic acid dihydrate (126 mg) in EtOH (2 mL) added. On standing at −200° C. overnight, the title product monooxalate salt precipitates as an orange solid (200 mg): mp 150–153° C.

EXAMPLE 70

4-[4-(4-Benzyl-piperidin-1-yl)-but-1-ynyl]-benzene-1,2-diamine

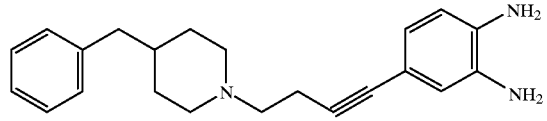

4-[4-(4-Benzyl-piperidin-1-yl)-but-1-ynyl]-2-nitro-phenylamine (crude product, example 69) (2.56 g, 7.0 mmol) is stirred in EtOH (52 mL) and water (8 mL) with conc. HCl (5 drops) and iron filings (3.75 g) at 75° C. for 2 hr. The mixture is filtered and evaporated. The residue is purified by medium-pressure column chromatography on silica gel eluting with 200:8:1 CH$_2$Cl$_2$:EtOH:NH$_4$OH to give the title compound as a beige solid (1.82 g): mp 141–142° C.

EXAMPLE 71

5-[4-(4-Benzyl-piperidin-1-yl)-but-1-ynyl]-1,3-dihydro-benzoimidazol-2-one

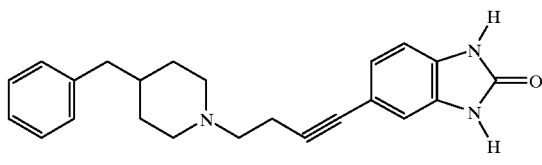

A mixture of 4-[4-(4-benzyl-piperidin-1-yl)-but-1-ynyl]-benzene-1,2-diamine (Example 70) (333 mg, 1 mmol) and carbonyl diimidazole (243 mg, 1.5 mmol) in THF (5 mL) is stirred at room temperature for 1 hr. A precipitate forms; the mixture is diluted with ether (10 mL), filtered and the solid washed with ether to give the title compound as a white powder (233 mg): mp 221–223° C.

EXAMPLE 72

N-{4-[4-(4-Phenylsulfanyl-piperidin-1-yl)-but-1-ynyl]-phenyl}-methanesulfonamide

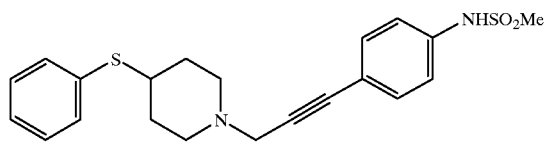

The above described product is prepared in a manner similar to that described for Example 41.

EXAMPLE 73

4-[3-(4-Benzyl-piperidin-1-yl)-prop-1-ynyl]-benzamide

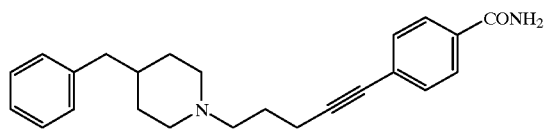

The above described product is prepared in a manner similar to that described for Example 41.

EXAMPLE 74

4-[3-(4-Benzyl-piperidin-1-yl)-prop-1-ynyl]-benzenesulfonamide

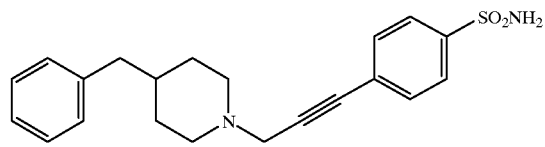

The above described product is prepared in a manner similar to that described for Example 41.

EXAMPLE 75

5-[4-(4-Benzyl-piperidin-1-yl)-but-1-ynyl]-1H-indole-2,3-dione

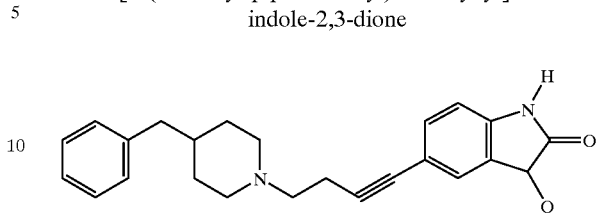

A mixture of 4-benzyl-1-(3-butynyl)piperidine (904 mg, 4 mmol), $Et_3N$ (4 mL), CuI (76 mg, 0.4 mmol) and $Pd(PPh_3)_2Cl_2$ (41 mg, 0.1 mmol) in DMF (10 mL) is stirred at room temperature under $N_2$ for 30 min. 5-Iodoisatin (546 mg, 2 mmol) is added and stirring continued overnight. The mixture is evaporated and the residue purified by medium-pressure column chromatography on silica gel eluting with 50% EtOAc/hexanes (+1% $Et_3N$) to give an orange solid (238 mg). The solid is recrystallized from hot 90:10 isopropanol:water to give the title compound as orange crystals (152 mg): mp 140–141° C.

EXAMPLE 76

4-(4-Methylbenzyl)-4-hydroxy-1-(but-3-yn-1-yl)piperidine

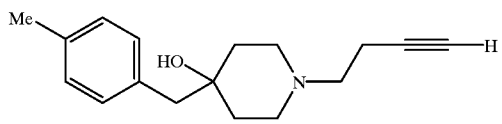

A mixture of 4-methyl-4-hydroxybenzylpiperidine hydrocholoride (1.3 g, 5.4 mmol), 1-butyn-4-yl methanesulfonate (0.96 g, 6.5 mmol), potassium carbonate (2.5 g, 18 mmol) in 50 mL of acetonitrile was allowed to reflux for 12 hrs. The inorganic salt was removed through a short column of silica gel and washed with ethyl acetate (3×30 mL). Evaporation of solvents gave a residue, which was purified by flash chromatography (50% EtOAc in hexane), giving 0.90 g (65%) of the title compound as a pale yellow oil. $^1$H NMR ($CDCl_3$) 1.258 (m, 2 H), 1.883 (m, 2 H), 1.962 (m, 3 H), 2.040 (m, 2 H), 2.342 (s, 3 H), 2.399 (m, 2 H), 2.611 (m, 3 H), 2.708 (m, 2 H), 7.060–7.135 (m, 4 H).

EXAMPLE 77

1-(1-(4-Aminophenyl)-1-butyn-4-yl)-4-hydroxy-4-(4-methylbenzyl)piperidine

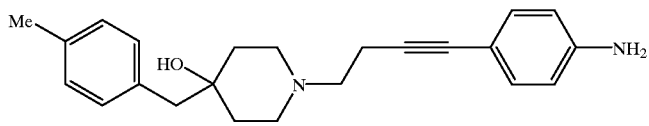

To a solution of 4-hydroxy-4-(4-methylbenzyl)-1-(1-but-3-yn-1-yl) piperidine (450 mg. 1.75 mmol) and 4-iodoaniline (383 mg., 1.75 mmol) in 15 mL. of pyrrolidine was added 75 mg of $Pd(PPh_3)_4$. The resulting solution was allowed to stir at rt for 24 h. The solvent was evaporated in vacuo and the residue was purified by flash chromatography (20% EtOAc in hexane), giving 325 mg (54%) of the title compound as a brown oil. $^1H$ NMR ($CDCl_3$) 1.647 (m, 3 H), 1.880 (m, 2 H), 2.046 (m, 2 H), 2.326 (s, 3 H), 2.592 (m, 2 H), s.712 (m, 4 H), 2.454 (m, 4 H), 3.729 (s, 2 H), 6.578 (m, 2 H), 7.107–7.190 (m, 6 H).

By following the general procedures set forth above, the additional inventive compounds shown in Tables 1 and 2 can be prepared.

TABLE 1

| Example | $R^5$ | X | $R^4$ | n | $Ar^2$ |
|---|---|---|---|---|---|
| 78 | H | $CH_2$ | H | 1 | benzoxazolone |
| 79 | F | S | H | 1 | methylindolinone |
| 80 | Me | O | H | 2 | methylbenzimidazolone |
| 81 | Cl | S | H | 2 | methylbenzothiadiazole S-oxide |
| 82 | MeO | $CH_2$ | OH | 1 | methylbenzimidazole |
| 83 | F | $CH_2$ | H | 3 | methylindole |
| 84 | Et | O | H | 1 | methylisatin |
| 85 | Cl | O | H | 2 | methylbenzotriazole |
| 86 | Me | $CH_2$ | H | 1 | methylindazole |
| 87 | H | S | H | 3 | methyltetrahydroquinoxaline |
| 88 | MeO | $CH_2$ | OH | 2 | methylquinoxalinedione |

TABLE 1-continued

![structure: R5-C6H4-X-C(R4)(piperidine-N-(CH2)n-C≡C-Ar2)]

| Example | R⁵ | X | R⁴ | n | Ar² |
|---|---|---|---|---|---|
| 89 | F | O | H | 1 | 6-methyl-4(1H)-quinolinone |
| 90 | F | CH₂ | H | 0 | 6-methyl-3,4-dihydroquinazolin-2(1H)-one |
| 91 | Cl | CH₂ | H | 1 | 7-methyl-5-methyl-1H-benzo[e][1,4]diazepin-2(3H)-one |
| 92 | i-Pr | CH₂ | OH | 2 | 7-methyl-1H-benzo[e][1,4]diazepine-2,4(3H,5H)-dione |
| 93 | Me | S | H | 3 | 7-methyl-4,5-dihydro-1H-benzo[d][1,3]diazepin-2(3H)-one |
| 94 | OH | — | H | 2 | 5-methyl-2,1,3-benzothiadiazole 2,2-dioxide |
| 95 | H | CH₂ | OH | 1 | 1-methyl-1H-benzimidazol-2(3H)-one |
| 96 | Cl | O | H | 1 | 5-methyl-2-aminopyridine |
| 97 | F | CH₂ | H | 2 | 5-methyl-2-aminothiazole |

TABLE 2

![structure: Ar1-X-C(R4)(piperidine-N-(CH2)n-C≡C-C6H4-R6)]

| Example | Ar¹ | X | R⁴ | n | R⁶ |
|---|---|---|---|---|---|
| 98 | 6-methylbenzoxazol-2(3H)-one | CH₂ | H | 1 | H |
| 99 | 5-methylindolin-2-one | S | H | 1 | F |
| 100 | 6-methylbenzimidazol-2(3H)-one | — | H | 2 | Me |
| 101 | 5-methyl-benzo[1,2,5]thiadiazole S-oxide | S | H | 2 | Cl |
| 102 | 5-methyl-1H-benzimidazole | — | OH | 1 | MeO |

TABLE 2-continued
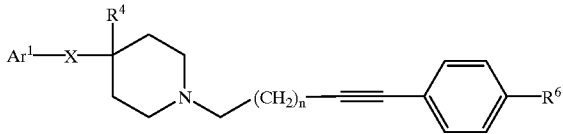
| Example | Ar¹ | X | R⁴ | n | R⁶ |
|---|---|---|---|---|---|
| 103 | 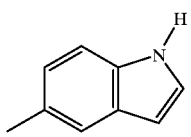 | — | H | 3 | F |
| 104 | 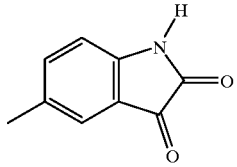 | O | H | 1 | Et |
| 105 | 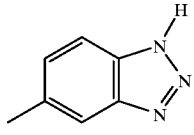 | — | H | 2 | Cl |
| 106 | 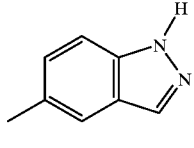 | $CH_2$ | H | 1 | Me |
| 107 | 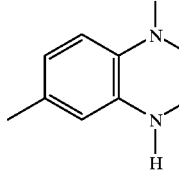 | S | H | 3 | H |
| 108 | 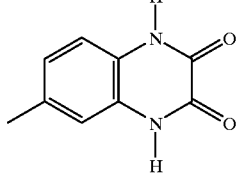 | — | OH | 2 | MeO |
| 109 | 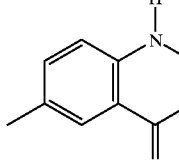 | O | H | 1 | F |
| 110 | 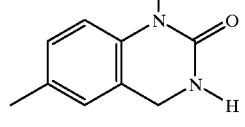 | $CH_2$ | H | 0 | F |
| 111 | 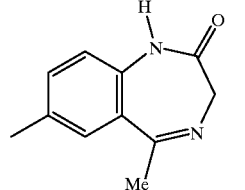 | — | H | 1 | Cl |
| 112 | 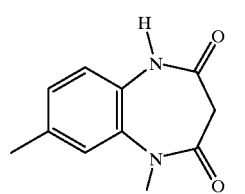 | $CH_2$ | OH | 2 | i-Pr |
| 113 | 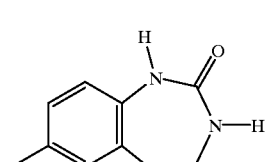 | S | H | 3 | Me |
| 114 | 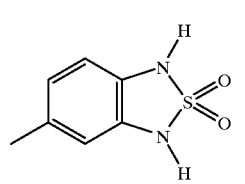 | — | H | 2 | OH |
| 115 | 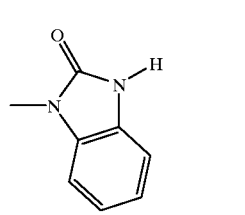 | $CH_2$ | OH | 1 | H |
| 116 | 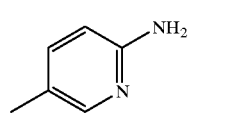 | O | H | 1 | Cl |
| 117 | 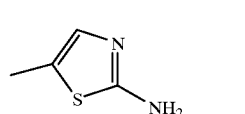 | — | H | 2 | F |

TABLE 2-continued

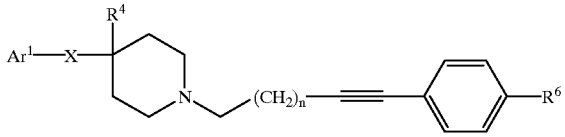

| Example | Ar¹ | X | R⁴ | n | R⁶ |
|---|---|---|---|---|---|
| 118 | (phenyl with NHSO₂Me) | — | OH | 1 | Cl |
| 119 | (phenyl with OH) | CH₂ | OH | 2 | H |

The potency of antagonism for the compounds of Examples 1, 7, 8, 11–16, 18, 25–35 and 37–77 described above in the expressed cloned NMDA subtypes and their anti-convulsant activity against maximal electroshock are shown below in Table 3.

TABLE 3

| Compound | Subunits (IC$_{50}$ ($\mu$M)) | | | | MES (ED$_{50}$) mg/kg |
| | 1A/2A | 1A/2B | 1A/2C | 1A/2D | |
|---|---|---|---|---|---|
| Ex. 1 | 150 | 1.3 | >300 | | |
| Ex. 7 | >100 | 3 | >100 | >100 | |
| Ex. 8 | >100 | 6 | >100 | >100 | 10.0 |
| Ex. 11 | >100 | 8.5 | >100 | >100 | |
| Ex. 12 | 50 | 14 | >100 | >100 | |
| Ex. 13 | 90 | 22 | >100 | >100 | |
| Ex. 14 | 40 | 30 | >100 | >100 | |
| Ex. 15 | 90 | 30 | >100 | >100 | |
| Ex. 16 | 85 | 45 | >100 | >100 | |
| Ex. 18 | >100 | 3 | >100 | | 3.5 |
| Ex. 25 | 40 | 14 | >100 | | |
| Ex. 26 | 21 | 5 | | | |
| Ex. 27 | 60 | 4 | >100 | | |
| Ex. 28 | 16 | 2 | 30 | | 10.0 |
| Ex. 29 | >100 | 1.8 | >100 | | |
| Ex. 30 | >100 | 0.33 | >100 | | 1.8 |
| Ex. 31 | >100 | 2 | >100 | | |
| Ex. 32 | 75 | 3.4 | >100 | | |
| Ex. 33 | 100 | 0.9 | >100 | | |
| Ex. 34 | >100 | 0.6 | >100 | | |
| Ex. 35 | >100 | 0.6 | >100 | | |
| Ex. 37 | 120 | 3.30 | >300 | | |
| Ex. 38 | >300 | 35.0 | >300 | | |
| Ex. 39 | 70.0 | 0.35 | >300 | | 2.5 |
| Ex. 40 | 120 | 5.00 | >300 | | |
| Ex. 41 | 130 | 3.00 | 250 | | |
| Ex. 42 | >300 | 0.14 | >300 | | 2.5 |
| Ex. 43 | 100 | 2.10 | >300 | | |
| Ex. 44 | 45.0 | 5.00 | 105 | | |
| Ex. 45 | 170 | 2.60 | >300 | | |
| Ex. 46 | >300 | 6.00 | >300 | | |
| EX. 47 | 160 | 120 | >300 | | |
| Ex. 48 | 45.0 | 3.20 | >300 | | |
| Ex. 49 | >300 | 37.0 | >300 | | |
| Ex. 50 | 300 | 3.00 | >300 | | |
| Ex. 51 | >300 | 1.20 | >300 | | |
| Ex. 52 | 15.0 | 0.40 | 200 | | |
| Ex. 53 | >300 | 0.45 | >300 | | 8.0 |
| Ex. 54 | 60.0 | 0.20 | >300 | | 6.5 |
| Ex. 55 | 200 | 23.0 | >300 | | |
| Ex. 56 | 150 | 0.20 | 150 | | |
| Ex. 57 | 150 | 3.00 | 300 | | |
| Ex. 58 | >300 | 40.0 | >300 | | |
| Ex. 59 | 21.0 | 0.70 | >300 | | >5 |
| Ex. 60 | >300 | 20.0 | >300 | | |
| Ex. 61 | 70.0 | 15.0 | >300 | | |
| Ex. 62 | 160 | 18.0 | 270 | | |
| Ex. 63 | 180 | 12.0 | >300 | | |
| Ex. 64 | >300 | 0.37 | >300 | | |
| Ex. 65 | >300 | 1.40 | >300 | | |
| Ex. 66 | 170 | 1.00 | 180 | | |
| Ex. 67 | 70.0 | 0.70 | 58.0 | | 6.0 |
| Ex. 68 | | 0.35 | | | |
| Ex. 69 | | 0.25 | | | |
| Ex. 70 | | 0.18 | | | |
| Ex. 71 | | 0.10 | | | |
| Ex. 72 | | 0.40 | | | |
| Ex. 73 | | 30.0 | | | |
| Ex. 74 | | 80.0 | | | |
| Ex. 75 | | 2.00 | | | |
| Ex. 76 | 280 | 1.0 | >300 | | |
| Ex. 77 | 70 | 0.4 | >300 | | 0.4 |
| † | 5 | 2.9 | 3 | | |
| ‡ | >100 | 8.5 | >100 | | |

† N-4-(1-(4-(3-aminophenyl)butyn-3-yl)piperidinyl)-2-oxobenzimidazol;
‡ -1-(4-(2-aminophenyl)-3-butynyl)-4-phenylpiperidine The data are the mean IC$_{50}$ values ($\mu$M) for inhibition of NMDA-activated membrane current responses. The data show that 4-substituted piperidine analogs of this invention exhibit selectivity for 2B subtype receptors compared to 2A, 2C and 2D subtype receptors.

In addition, compounds 8, 18, 28, 30, 39, 42, 53, 54 and 67 also demonstrated potent activity against maximal electroshock (MES) as shown in Table 3.

Other variations and modifications of this invention will be obvious to those skilled in this art. This invention is not limited except as set forth in the following claims.

What is claimed is:

1. A compound represented by the formula (I)

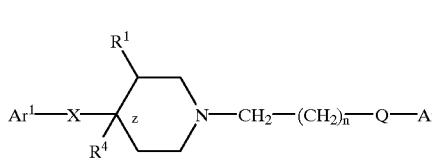

or a pharmaceutically acceptable salt thereof wherein
Ar¹ is aryl and Ar² is a bicyclic heteroaryl group, either of which may be independently substituted by hydrogen, hydroxy, alkyl, halogen, nitro, aryl, aralkyl, amino, a halogenated alkyl group, —NHAc, —NHSO₂Me, —N(SO₂Me)₂, —CONHalkyl, —SO₂NH₂, an alkylguanidine group, a lower alkyl amino group or a lower alkoxy group;
z is a single bond;
X is —(CHR2)m—, wherein each R2 is hydrogen and m is 1;
R1 is hydrogen or hydroxy;
n is 1 or 2;
Q is —C≡C—; and
R4 is hydrogen or hydroxy.

2. A compound according to claim 1, wherein Ar¹ is substituted or unsubstituted phenyl.

3. A compound according to claim 2, wherein Ar¹ is a halophenyl group.

4. A compound represented by the formula:

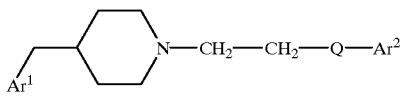

(IV)

or a pharmaceutically acceptable salt thereof wherein:
Ar1 is aryl and Ar2 is a bicyclic heteroaryl group, either of which may be independently substituted by hydrogen, hydroxy, alkyl, halogen, nitro, aryl, aralkyl, amino, a halogenated alkyl group, —NHAc, —NHSO₂Me, —N(SO₂Me)₂, —CONHalkyl, —SO₂NH₂, an alkylguanidine group, a lower alkyl amino group or a lower alkoxy group; and
Q is —C≡C—.

5. A compound represented by the formula:

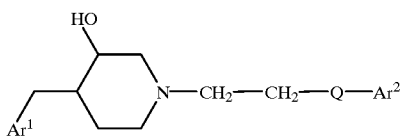

(V)

or a pharmaceutically acceptable salt thereof wherein:
Ar1 is aryl and Ar2 is a bicyclic heteroaryl group, either of which may be independently substituted by hydrogen, hydroxy, alkyl, halogen, nitro, aryl, aralkyl, amino, a halogenated alkyl group, —NHAc, —NHSO₂Me, —N(SO₂Me)₂, —CONHalkyl, —SO₂NH₂, an alkylguanidine group, a lower alkyl amino group or a lower alkoxy group; and
Q is —C≡C—.

6. A compound according to claim 1, said compound selected from the group consisting of:
N-4-(1-(4-(3-Aminophenyl)butyn-3-yl)piperidinyl)-2-oxobenzimidazol;
1-(4-Benzo[1,3]dioxol-5-yl-but-3-ynyl)-4-benzyl-piperidine;
4-Benzyl-1-[4-(2,3-dihydro-benzo[1,4]dioxin-6-yl)-but-3-ynyl]-piperidine;
5-[4-(4-Benzyl-piperidin-1-yl)-but-1-ynyl]-1H-indole;
5-[4-(4-Benzyl-piperidin-1-yl)-but-1-ynyl]-1H-indazole;
5-[4-(4-Benzyl-piperidin-1-yl)-but-1-ynyl]-1,3-dihydro-benzoimidazol-2-one;
5-[4-(4-Benzyl-piperidin-1-yl)-but-1-ynyl]-1H-indole-2,3-dione;
and a pharmaceutically acceptable salt thereof.

7. A pharmaceutical composition useful for treating disorders responsive to the selective blockade of N-methyl-D-aspartate receptor subtypes selected from the group consisting of stroke, cerebral ischemia, central nervous system trauma, hypoglycemia, neurodegenerative disorders, anxiety, migraine headaches, convulsions, aminoglycoside antibiotics-induced hearing loss, chronic pain, psychosis, glaucoma, CMV retinitis, opioid tolerance or withdrawal and urinary incontinence, said compositions comprising a pharmaceutically acceptable carrier or diluent and a therapeutically effective amount of at least one compound of claim 1.

8. A method for treating disorders responsive to the selective blockade of N-methyl-D-aspartate receptor subtypes in an animal suffering therefrom, said disorders selected from the group consisting of stroke, cerebral ischemia, central nervous system trauma, hypoglycemia, neurodegenerative disorders, anxiety, migraine headaches, convulsions, aminoglycoside antibiotics-induced hearing lose, chronic Pain, psychosis, glaucoma, CMV retinitis, opioid tolerance or withdrawal and urinary incontinence, which method comprises administering in unit dosage form of at least one compound represented by the formula (I):

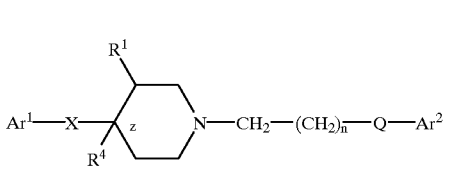

(I)

or a pharmaceutically acceptable salt thereof wherein
Ar¹ is aryl and Ar² is a bicyclic heteroaryl group, either of which may be independently substituted by hydrogen, hydroxy, alkyl, halogen, nitro, aryl, aralkyl, amino, a halogenated alkyl group, —NHAc, —NHSO₂Me, —N(SO₂Me)₂, —CONHalkyl, —SO₂NH₂, an alkylguanidine group, a lower alkyl amino group or a lower alkoxy group;
z is a single bond;
X is —(CHR²)$_m$—, wherein each R² is hydrogen and m is 1;
R¹ is hydrogen or hydroxy;
n is 1 or 2;
Q is —C≡C—; and
R⁴ is hydrogen or hydroxy.

9. A method for treating disorders responsive to the selective blockade of N-methyl-D-aspartate receptor subtypes in an animal suffering therefrom, said disorder selected from the group consisting of stroke, cerebral ischemia, central nervous system trauma, hypoglycemia, neurodegenerative disorders, anxiety, migraine headaches convulsions, aminoglycoside antibiotics-induced hearing loss, chronic pain, psychosis, glaucoma, CMV retinitis, opioid tolerance or withdrawal and urinary incontinence, which method comprises administering in unit dosage form of at least one compound represented by the formula:

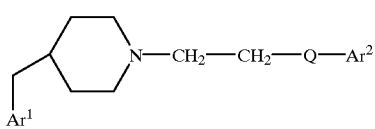

(IV)

or a pharmaceutically acceptable salt thereof wherein:
Ar¹ is aryl and Ar² is a bicyclic heteroaryl group, either of which may be independently substituted by hydrogen, hydroxy, alkyl, halogen, nitro, aryl, aralkyl, amino, a halogenated alkyl group, —NHAc, —NHSO₂Me, —N(SO₂Me)₂, —CONHalkyl, —SO₂NH₂, an alkylguanidine group, a lower alkyl amino group or a lower alkoxy group; and
Q is —C≡C—.

10. A method for treating disorders responsive to the selective blockade of N-methyl-D-aspartate receptor subtypes in an animal suffering therefrom, said disorder selected from the group consisting of stroke, cerebral ischemia, central nervous system trauma, hypoglycemia, neurodegenerative disorders, anxiety, migraine headaches, convulsions, aminoglycoside antibiotics-induced hearing loss, chronic pain, psychosis, glaucoma, CMV retinitis, opioid tolerance or withdrawal and urinary incontinence, which method comprises administering in unit dosage form of at least one compound represented by the formula:

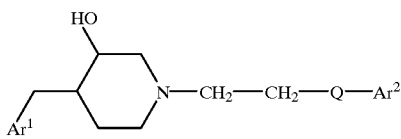

(V)

or a pharmaceutically acceptable salt thereof wherein:
$Ar^1$ is aryl and $Ar^2$ is a bicyclic heteroaryl group, either of which may be independently substituted by hydrogen, hydroxy, alkyl, halogen, nitro, aryl, aralkyl, amino, a halogenated alkyl group, —NHAc, —NHSO$_2$Me, —N(SO$_2$Me)$_2$, —CONHalkyl, —SO$_2$NH$_2$, an alkylguanidine group, a lower alkyl amino group or a lower alkoxy group; and
Q is —C≡C—.

11. A method for treating disorders responsive to the selective blockade of N-methyl-D-aspartate receptor subtypes in an animal suffering therefrom, said disorder selected from the group consisting of stroke, cerebral ischemia, central nervous system trauma, hypoglycemia, neurodegenerative disorders, anxiety, migraine headaches, convulsions, aminoglycoside antibiotics-induced hearing loss, chronic pain, psychosis, glaucoma, CMV retinitis, opioid tolerance or withdrawal and urinary incontinence, which method comprises administering in unit dosage form of at least one compound selected from the group consisting of:
N-4-(1-(4-(3-Aminophenyl)butyn-3-yl)piperidinyl)-2-oxobenzimidazol;
1-(4-Benzol[1,3]dioxol-5-yl-but-3-ynyl)-4-benzyl-piperidine;
4-Benzyl-1-[4-(2,3-dihydro-benzo[1,4]dioxin-6-yl)-but-3-ynyl]-piperidine;
5-[4-(4-Benzyl-piperidin-1-yl)-but-1-ynyl]-1H-indole;
5-[4-(4-Benzyl-piperidin-1-yl)-but-1-ynyl]-1H-indazole;
5-[4-(4-Benzyl-piperidin-1-yl)-but-1-ynyl]-1,3-dihydro-benzoimidazol-2-one;
5-[4-(4-Benzyl-piperidin-1-yl)-but-1-ynyl]-1H-indole-2,3-dione;
and a pharmaceutically acceptable salt thereof.

12. A method for preparing the compound represented by formula I:

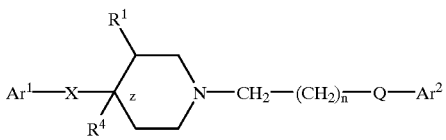

(I)

or a pharmaceutically acceptable salt thereof wherein $Ar^1$ is aryl and $Ar^2$ is a bicyclic heteroaryl group, either of which may be independently substituted by hydrogen, hydroxy, alkyl, halogen, nitro, aryl, aralkyl, amino, a halogenated alkyl group, —NHAc, —NHSO$_2$Me, —N(SO$_2$Me)$_2$, —CONHalkyl, —SO$_2$NH$_2$, an alkylguanidine group, a lower alkyl amino group or a lower alkoxy group;
z is a single bond;
X is —(CHR$^2$)$_m$—, wherein each $R^2$ is hydrogen and m is 1;
$R^1$ is hydrogen or hydroxy;
n is 1 or 2;
Q is —C≡C—; and
$R^4$ is hydrogen or hydroxy said method comprising the steps of:
(a) reacting, in the presence of a base, a compound of formula VII

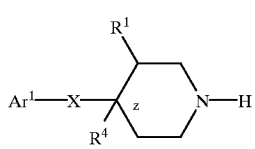

VII wherein $Ar^1$, X, $R^1$, $R^4$ and z are as previously described, with a compound of formula IX

IX wherein n and Q are as previously described and L is a leaving group to afford a compound of formula X

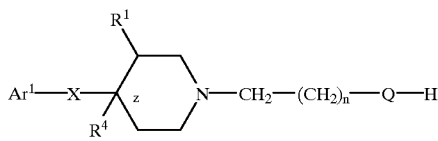

X wherein $Ar^1$, X, $R^1$, $R^4$, z, n and Q are as previously described; and
(b) reacting the compound of formula X with Ar$^2$Y, wherein $Ar^2$ is as previously defined and Y is a transmetalation group, in the presence of a palladium catalyst to afford the compound of formula I.

13. A method according to claim 12, wherein said transmetalation group is selected from the group consisting of Br, I, B(OH)$_2$ and HgCl.

14. A method for preparing the compound represented by formula I:

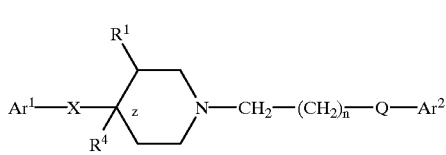

(I)

or a pharmaceutically acceptable salt thereof wherein $Ar^1$ is aryl and $Ar^2$ is a bicyclic heteroaryl group, either of which may be independently substituted by hydrogen, hydroxy, alkyl, halogen, nitro, aryl, aralkyl, amino, a halogenated alkyl group, —NHAc, —NHSO2Me, —N(SO2Me)2, —CONHalkyl, —SO2NH2, an alkylguanidine group, a lower alkyl amino group or a lower alkoxy group;
z is a single bond;
X is —(CHR$^2$)$_m$—, wherein each $R^2$ is hydrogen and m is 1;

$R^1$ is hydrogen or hydroxy;

n is 1 or 2;

Q is —C≡C—; and $R^4$ is hydrogen or hydroxy said method comprising the steps of:

(a) reacting, in the presence of a palladium catalyst, a compound of formula XI

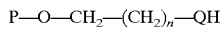  XI wherein P is a general protecting group, and n and Q are as previously described, with $Ar^2Y$, wherein $Ar^2$ is as previously defined and Y is a transmetalation group, to afford a compound represented by formula XII

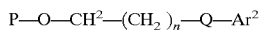  XII wherein P, n, Q and Ar2 are as previously described;

(b) deprotecting the compound of formula XII to give a compound represented by formula XIII

  XIII wherein n, Q and $Ar^2$ are as previously described;

(c) reacting the compound of formula XIII with an activating compound, in the presence of base, to give the compound represented by formula XIV $A-CH_2-(CH_2)_n-Q-Ar^2$  XIV wherein A is an activating group, and n, Q and $Ar^2$ are as previously described; and (d) reacting, in the presence of a base, the compound of formula XIV with the compound of formula VII

VII

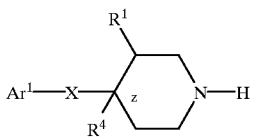

wherein $Ar^1$, X, $R^1$, $R^4$ and z are as previously described, to give the compound of formula I.

15. A method according to claim 14, wherein said transmetalation group is selected from the group consisting of Br, I, $B(OH)_2$ and HgCl.

16. A method according to claim 15, wherein said activating compound is selected from the group consisting of tosylates, triflates, mesylates and diethylazadicarboxylate.

* * * * *